(12) United States Patent
Behm et al.

(10) Patent No.: US 8,859,845 B2
(45) Date of Patent: Oct. 14, 2014

(54) METHODS AND COMPOSITIONS FOR SELECTING SOYBEAN PLANTS RESISTANT TO PHYTOPHTHORA ROOT ROT

(75) Inventors: James Behm, Findlay, OH (US); Kunsheng Wu, Ballwin, MO (US); John Tamulonis, Nevada, IA (US); Vergel Concibido, Maryland Heights, MO (US); Jennifer Yates, Elkton, MD (US)

(73) Assignee: Monsanto Technology LLC, St. Louis, MO (US)

( * ) Notice: Subject to any disclaimer, the term of this patent is extended or adjusted under 35 U.S.C. 154(b) by 901 days.

(21) Appl. No.: 12/103,944

(22) Filed: Apr. 16, 2008

(65) Prior Publication Data

US 2008/0263720 A1    Oct. 23, 2008

Related U.S. Application Data

(60) Provisional application No. 60/925,475, filed on Apr. 20, 2007.

(51) Int. Cl.
| | |
|---|---|
| A01H 1/00 | (2006.01) |
| A01H 5/00 | (2006.01) |
| C12N 5/04 | (2006.01) |
| C12N 15/82 | (2006.01) |
| C12Q 1/68 | (2006.01) |
| A01H 1/04 | (2006.01) |

(52) U.S. Cl.
CPC ............... A01H 1/04 (2013.01); C12Q 1/6895 (2013.01)
USPC ........... 800/265; 800/267; 800/279; 800/278; 800/312; 435/6.11

(58) Field of Classification Search
USPC ........................... 800/267, 279, 312; 435/6.11
See application file for complete search history.

(56) References Cited

U.S. PATENT DOCUMENTS

| | | | |
|---|---|---|---|
| 6,828,490 B1 * | 12/2004 | Fabrizius et al. ............. | 800/312 |
| 7,256,323 B1 | 8/2007 | Bhattacharyya | |
| 7,381,862 B2 | 6/2008 | St. Martin et al. | |
| 7,435,873 B2 | 10/2008 | St. Martin et al. | |
| 7,507,874 B2 | 3/2009 | Han et al. | |
| 2006/0059580 A1 | 3/2006 | Han et al. | |
| 2006/0288444 A1 | 12/2006 | McCarroll et al. | |

FOREIGN PATENT DOCUMENTS

| | | |
|---|---|---|
| CA | 2 269 215 | 10/1999 |
| WO | 2006017833 | 2/2006 |

OTHER PUBLICATIONS

Bhattacharyya, et al., Identification of a large cluster of coiled coil-nucleotide binding site-leucine rich repeat-type genes from the Rps1 region containing *Phytophthora* resistance genes in soybean, Theor. Appl. Genet. 111:75-86 (2005) Duplicate.
Cregan et al., An Integrated Genetic Linkage Map of the Soybean Genome, Crop Science 39:1464-1490 (2004).
Demirbas, et al., Simple Sequence Repeat Markers Linked to the Soybean Rps Genes for *Phytophthora* Resistance, Crop Science 41:1220-1227 (2001.
Ferro, et al., Evaluation of Soybean Cultivars with the Rps1k Gene for Partial Resistance or Field Tolerance to *Phytophthora sojae*, Crop Science 46:2427-2436 (2006).
Valer, et al., Spatial and temporal expression patterns of Avr1b- 1 and defense-related genes in soybean plants upon infection with *Phytophthora sojae*, FMS Microbiol. Lett. 265:60-68 (2006).
Zhang, et al., An Integrated BAC and Genmoe Sequence Physical Map of *Phytophthora sojae*, MPMI 19:1302-1310 (2006).
Bhattacharyya, et al., Identification of a large cluster of coiled coil-nucleotide binding site-leucine rich repeat-type genes from the Rps1 region containing *Phytophthora* resistance genes in soybean, Theor. App. Genet. 111:75-86 (2005).
Demirbas et al., Simple Sequence Repeat Markers Linked to the Soybean Rps Genes for *Phytophthora* Resistance, Crop Science 41:1220-1227 (2001).
Diers et al., Mapping *Phytophthora* Resistance Loci in Soybean with Restriction Fragment Length Polymorphism Markers, Crop Science 32:377-383 (1992).
Ferro et al., Evaluation of Soybean Cultivars with the Rps1k Gene for Partial Resistance or Field Tolerance to *Phytophthora sojae*, Crop Science 46:2427-2436 (2006).
Gardner et al., Physical Map Location of the Rps1-k Allele in Soybean, Crop Science 41-1435-1438 (2001).
Hegstad et al., Identifying Resistance to *Phytophthora sojae* in Selected Soybean Accessions Using RPLP Techniques, Crop Science 38:50-55 (1998).
Kasuga e tal., High Resolution Genetic and Physical Mapping of Molecular Markers Linked to the *Phytophthora* Resistance Gene Rps1-k in Soybean, MPMI 10:1035-1044 (1997).
Burnham et al., "Rps8, a new locus in soybean for resistance to *Phytophthora sojae*," Crop Sci 43:101-105, 2003.

* cited by examiner

*Primary Examiner* — Medina A Ibrahim
(74) *Attorney, Agent, or Firm* — Dentons US LLP; Lawrence M. Lavin, Jr.

(57) ABSTRACT

The present invention relates to the field of plant breeding and disease resistance. More specifically, the invention includes a method for breeding soybean plants containing quantitative trail loci (QTL) for resistance the *Phytophthora* root rot (PRR) caused by *Phytophthora sojae*. The invention further includes the use of molecular markers in the introgression of PRR resistance QTL into soybean plants.

4 Claims, No Drawings

METHODS AND COMPOSITIONS FOR SELECTING SOYBEAN PLANTS RESISTANT TO PHYTOPHTHORA ROOT ROT

CROSS-REFERENCE TO RELATED APPLICATIONS

This application claims the benefit under 35 U.S.C. §119(e) of U.S. Provisional Application No. 60/925,475, filed Apr. 20, 2007, the disclosure of which application is incorporated herein by reference in its entirety.

INCORPORATION OF THE SEQUENCE LISTING

A sequence listing containing the file named "Sequence Listing.txt" which is 52,115 bytes (measured in Microsoft Windows®) and created on Apr. 7, 2008, comprises 116 nucleotide sequences, and is herein incorporated by reference in its entirety.

FIELD OF THE INVENTION

The present invention is in the field of plant breeding and disease resistance. More specifically, the invention includes a method of breeding plants from the genus *Glycine* containing quantitative trait loci (QTL) that are associated with disease resistance to the pathogen *Phytophthora sojae* (Kauffman & Gerdemann). The invention relates to the use of genetic markers to identify QTL for disease resistance. The invention further relates to the use of genetic markers for the introgression of resistance to *Phytophthora sojae* into elite germplasm in a breeding program.

BACKGROUND OF THE INVENTION

*Phytophthora sojae* (Kauffman & Gerdemann) is an oomycete pathogen which causes extensive damage to roots and stems of soybean plants (*Glycine max*) (Zhang et al., *MPMI*, 19:1302-1310 (2006)). Symptoms of *Phytophthora* Root Rot (PRR) caused by *P. sojae* include yellowing and wilting of leaves and browning of lower stems and branches (Demirbas et al., *Crop Sci.* 41:1220-1227 (2001)). PRR results in annual worldwide soybean crop losses of $1 to $2 billion (Zhang et al., *MPMI*, 19: 1302-1310 (2006)). Soybean PRR resistance or susceptibility depends on a system of signaling between pathogen and host. Certain quantitative trait loci (QTL) can confer resistance to PRR. Pathogen avirulence (Avr) and host resistance (Rps) quantitative trait loci determine the interaction of different *P. sojae* races and soybean cultivars (Valer et al., *FEMS Microbiol Lett.*, 265:60-68 (2006)). Eight loci have been identified which provide race-specific resistance to PRR, and two of these loci, Rps1 and Rps3, have been identified as having multiple alleles which are designated by a letter following the locus number (Ferro et al., *Crop Sci*, 46:2427-2436 (2006)). The Rps1 locus includes, for example, Rps1a, Rps1b, Rps1c, Rps1d, and Rps1k, and the Rps3 locus includes, for example, Rps3a, Rps3b, and Rps3c. Map-based cloning has attempted to characterize the Rps1k region (Bhattacharyya, M. K. et al., *Theor Appl Genet*, 111:75-86 (2005), U.S. Pat. No. 7,256,323). Planting soybean cultivars with race-specific resistance genes has been the primary means of controlling PRR (Ferro et al., *Crop Sci.*, 46:2427-2436 (2006)). Over fifty *P. sojae* races have been identified, and Rps loci can provide resistance to more than one *P. sojae* race. Examples include, but are not limited to, the following: Rps1k can provide resistance to *P. sojae* races 1 and 4, Rps1c can provide resistance to *P. sojae* races 1 and 3, and Rps8 can provide resistance to *P. sojae* races 1, 4, 7, and 25. Plant breeders are able to use molecular markers as an indirect means to select plants with alleles resistant to PRR races of concern (Demirbas et al., *Crop Sci.* 41:1220-1227 (2001)).

Breeding for PRR resistant soybeans can be greatly facilitated by the use of marker-assisted selection for PRR resistance alleles. Genetic markers used in soybean breeding programs to detect, select for, and introgress PRR resistant plants have included simple sequence repeats (SSRs), restriction fragment length polymorphisms (RFLPs), and single nucleotide polymorphisms (SNPs). SSR and SNP markers have been provided for PRR resistance loci on Linkage Groups B1, G, K, and M (U.S. patent application Ser. No. 11/199,819 (filed Aug. 8, 2005)). RFLP markers, SSR markers, and isozyme markers have been provided for PRR resistance loci located on Linkage Group A2 (U.S. patent application Ser. No. 10/436,376 (filed May 12, 2003)). SSR markers have been provided for PRR resistance loci located on Linkage Group F (U.S. patent application Ser. No. 10/778,018 (filed Feb. 12, 2004)). Linkage groups are described by Cregan et al. (*Crop Sci.* 39:1464-1490 (1999)). To date, a SNP-based marker set for Rps1 on Linkage Group N, Rps3 on Linkage Group F, and Rps8 on Linkage Group F is lacking.

Of the classes of markers, SNPs have characteristics which make them preferential to other genetic markers in detecting, selecting for, and introgressing PRR resistance in a soybean plant. SNPs are preferred because technologies are available for automated, high-throughput screening of SNP markers, which can decrease the time to select for and introgress PRR resistance in soybean plants. Further, SNP markers are ideal because the likelihood that a particular SNP allele is derived from independent origins in the extant population of a particular species is very low. As such, SNP markers are useful for tracking and assisting introgression of PRR resistance alleles, particularly in the case of PRR resistance haplotypes. A need exists for a SNP based marker set to screen for resistance to PRR races with agronomic importance. Rps1, Rps3, and Rps8 provide resistance to PRR races that are a significant source of damage to soybean crops. The present invention provides a SNP-based marker set for Rps1 on Linkage Group N, Rps3 on Linkage Group F, and Rps8 on Linkage Group F.

The present invention provides and includes a method for screening and selecting a soybean plant comprising at least one PRR resistance QTL. The invention includes SNP markers for the detection of, selection for, and introgression of PRR resistance QTL from PRR resistant soybean plants.

SUMMARY OF THE INVENTION

The present invention includes a method of selecting for and introgressing an allele into a soybean plant comprising (A) crossing at least one PRR resistant soybean plant with at least one other soybean plant in order to form a population, (B) screening said population with at least one nucleic acid marker selected from the group comprising SEQ ID NO: 1 to SEQ ID NO: 16 and SEQ ID NO: 81 to SEQ ID NO: 84, (C) selecting from said population one or more soybean plants comprising at least one genotype corresponding to a PRR resistant soybean plant.

The present invention further comprises an elite soybean plant produced by such method.

The present invention includes a method of introgressing an allele into a soybean plant comprising: (A) crossing at least one PRR resistant soybean plant with at least one other soybean plant in order to form a population, (B) screening said population with at least one nucleic acid marker, (C) selecting from said population one or more soybean plants comprising a haplotype associated with PRR resistance, wherein said PRR resistance haplotype is selected from the group consisting of 1, 2, or 3 PRR resistant loci where one or more haplotypes at one or more loci are selected from the group of Rps1, Rps3, and Rps8, and the one or more haplotypes are selected based on the haplotype of the PRR resistant soybean plants.

The present invention further comprises an elite soybean plant produced by said method.

The present invention includes a substantially purified nucleic acid molecule comprising a nucleic acid sequence selected from the group consisting of SEQ ID NO: 1 to SEQ ID NO: 116.

Further, the present invention provides assays for detection of the PRR resistance QTLs, Rps1, Rps3, and Rps8.

BRIEF DESCRIPTION OF THE NUCLEIC ACID SEQUENCES

SEQ ID NO: 1 is a genomic sequence derived from *Glycine max* associated with the PRR resistance locus Rps1.

SEQ ID NO: 2 is a genomic sequence derived from *Glycine max* associated with the PRR resistance locus Rps1.

SEQ ID NO: 3 is a genomic sequence derived from *Glycine max* associated with the PRR resistance locus Rps1.

SEQ ID NO: 4 is a genomic sequence derived from *Glycine max* associated with the PRR resistance locus Rps1.

SEQ ID NO: 5 is a genomic sequence derived from *Glycine max* associated with the PRR resistance locus Rps1.

SEQ ID NO: 6 is a genomic sequence derived from *Glycine max* associated with the PRR resistance locus Rps1.

SEQ ID NO: 7 is a genomic sequence derived from *Glycine max* associated with the PRR resistance locus Rps1.

SEQ ID NO: 8 is a genomic sequence derived from *Glycine max* associated with the PRR resistance locus Rps1.

SEQ ID NO: 9 is a genomic sequence derived from *Glycine max* associated with the PRR resistance locus Rps1.

SEQ ID NO: 10 is a genomic sequence derived from *Glycine max* associated with the PRR resistance locus Rps1.

SEQ ID NO: 11 is a genomic sequence derived from *Glycine max* associated with the PRR resistance loci Rps3 and Rps8.

SEQ ID NO: 12 is a genomic sequence derived from *Glycine max* associated with the PRR resistance loci Rps3 and Rps8.

SEQ ID NO: 13 is a genomic sequence derived from *Glycine max* associated with the PRR resistance loci Rps3 and Rps8.

SEQ ID NO: 14 is a genomic sequence derived from *Glycine max* associated with the PRR resistance loci Rps3 and Rps8.

SEQ ID NO: 15 is a genomic sequence derived from *Glycine max* associated with the PRR resistance loci Rps3 and Rps8.

SEQ ID NO: 16 is a genomic sequence derived from *Glycine max* associated with the PRR resistance loci Rps3 and Rps8.

SEQ ID NO: 17 is a forward PCR primer for amplifying SEQ ID NO: 1.

SEQ ID NO: 18 is a reverse PCR primer for amplifying SEQ ID NO: 1.

SEQ ID NO: 19 is a forward PCR primer for amplifying SEQ ID NO: 2.

SEQ ID NO: 20 is a reverse PCR primer for amplifying SEQ ID NO: 2.

SEQ ID NO: 21 is a forward PCR primer for amplifying SEQ ID NO: 3.

SEQ ID NO: 22 is a reverse PCR primer for amplifying SEQ ID NO: 3.

SEQ ID NO: 23 is a forward PCR primer for amplifying SEQ ID NO: 4.

SEQ ID NO: 24 is a reverse PCR primer for amplifying SEQ ID NO: 4.

SEQ ID NO: 25 is a forward PCR primer for amplifying SEQ ID NO: 5.

SEQ ID NO: 26 is a reverse PCR primer for amplifying SEQ ID NO: 5.

SEQ ID NO: 27 is a forward PCR primer for amplifying SEQ ID NO: 6.

SEQ ID NO: 28 is a reverse PCR primer for amplifying SEQ ID NO: 6.

SEQ ID NO: 29 is a forward PCR primer for amplifying SEQ ID NO: 7.

SEQ ID NO: 30 is a reverse PCR primer for amplifying SEQ ID NO: 7.

SEQ ID NO: 31 is a forward PCR primer for amplifying SEQ ID NO: 8.

SEQ ID NO: 32 is a reverse PCR primer for amplifying SEQ ID NO: 8.

SEQ ID NO: 33 is a forward PCR primer for amplifying SEQ ID NO: 9.

SEQ ID NO: 34 is a reverse PCR primer for amplifying SEQ ID NO: 9.

SEQ ID NO: 35 is a forward PCR primer for amplifying SEQ ID NO: 10.

SEQ ID NO: 36 is a reverse PCR primer for amplifying SEQ ID NO: 10.

SEQ ID NO: 37 is a forward PCR primer for amplifying SEQ ID NO: 11.

SEQ ID NO: 38 is a reverse PCR primer for amplifying SEQ ID NO: 11.

SEQ ID NO: 39 is a forward PCR primer for amplifying SEQ ID NO: 12.

SEQ ID NO: 40 is a reverse PCR primer for amplifying SEQ ID NO: 12.

SEQ ID NO: 41 is a forward PCR primer for amplifying SEQ ID NO: 13.

SEQ ID NO: 42 is a reverse PCR primer for amplifying SEQ ID NO: 13.

SEQ ID NO: 43 is a forward PCR primer for amplifying SEQ ID NO: 14.

SEQ ID NO: 44 is a reverse PCR primer for amplifying SEQ ID NO: 14.

SEQ ID NO: 45 is a forward PCR primer for amplifying SEQ ID NO: 15.

SEQ ID NO: 46 is a reverse PCR primer for amplifying SEQ ID NO: 15.

SEQ ID NO: 47 is a forward PCR primer for amplifying SEQ ID NO: 16.

SEQ ID NO: 48 is a reverse PCR primer for amplifying SEQ ID NO: 16.

SEQ ID NO: 49 is a probe for detecting the PRR resistance locus of SEQ ID NO: 1.

SEQ ID NO: 50 is a second probe for detecting the PRR resistance locus of SEQ ID NO: 1.

SEQ ID NO: 51 is a probe for detecting the PRR resistance locus of SEQ ID NO: 2.

SEQ ID NO: 52 is a second probe for detecting the PRR resistance locus of SEQ ID NO:2.

SEQ ID NO: 53 is a probe for detecting the PRR resistance locus of SEQ ID NO: 3.

SEQ ID NO: 54 is a second probe for detecting the PRR resistance locus of SEQ ID NO:3.

SEQ ID NO: 55 is a probe for detecting the PRR resistance locus of SEQ ID NO: 4.

SEQ ID NO: 56 is a second probe for detecting the PRR resistance locus of SEQ ID NO: 4.

SEQ ID NO: 57 is a probe for detecting the PRR resistance locus of SEQ ID NO: 5.

SEQ ID NO: 58 is a second probe for detecting the PRR resistance locus of SEQ ID NO: 5.

SEQ ID NO: 59 is a probe for detecting the PRR resistance locus of SEQ ID NO: 6.

SEQ ID NO: 60 is a second probe for detecting the PRR resistance locus of SEQ ID NO:6.

SEQ ID NO: 61 is a probe for detecting the PRR resistance locus of SEQ ID NO: 7.

SEQ ID NO: 62 is a second probe for detecting the PRR resistance locus of SEQ ID NO: 7.

SEQ ID NO: 63 is a probe for detecting the PRR resistance locus of SEQ ID NO: 8.

SEQ ID NO: 64 is a second probe for detecting the PRR resistance locus of SEQ ID NO: 8.

SEQ ID NO: 65 is a probe for detecting the PRR resistance locus of SEQ ID NO: 9.

SEQ ID NO: 66 is a second probe for detecting the PRR resistance locus of SEQ ID NO:9.

SEQ ID NO: 67 is a probe for detecting the PRR resistance locus of SEQ ID NO: 10.

SEQ ID NO: 68 is a second probe for detecting the PRR resistance locus of SEQ ID NO: 10.

SEQ ID NO: 69 is a probe for detecting the PRR resistance loci of SEQ ID NO: 11.

SEQ ID NO: 70 is a second probe for detecting the PRR resistance loci of SEQ ID NO: 11.

SEQ ID NO: 71 is a probe for detecting the PRR resistance loci of SEQ ID NO: 12.

SEQ ID NO: 72 is a second probe for detecting the PRR resistance loci of SEQ ID NO: 12.

SEQ ID NO: 73 is a probe for detecting the PRR resistance loci of SEQ ID NO: 13.

SEQ ID NO: 74 is a second probe for detecting the PRR resistance loci of SEQ ID NO: 13.

SEQ ID NO: 75 is a probe for detecting the PRR resistance loci of SEQ ID NO: 14.

SEQ ID NO: 76 is a second probe for detecting the PRR resistance loci of SEQ ID NO: 14.

SEQ ID NO: 77 is a probe for detecting the PRR resistance loci of SEQ ID NO: 15.

SEQ ID NO: 78 is a second probe for detecting the PRR resistance loci of SEQ ID NO: 15.

SEQ ID NO: 79 is a probe for detecting the PRR resistance loci of SEQ ID NO: 16.

SEQ ID NO: 80 is a second probe for detecting the PRR resistance loci of SEQ ID NO: 16.

SEQ ID NO: 81 is a genomic sequence derived from *Glycine max* associated with the PRR resistance locus Rps1.

SEQ ID NO: 82 is a genomic sequence derived from *Glycine max* associated with the PRR resistance locus Rps1.

SEQ ID NO: 83 is a genomic sequence derived from *Glycine max* associated with the PRR resistance locus Rps1.

SEQ ID NO: 84 is a genomic sequence derived from *Glycine max* associated with the PRR resistance locus Rps1.

SEQ ID NO: 85 is a forward PCR primer for amplifying SEQ ID NO: 81.

SEQ ID NO: 86 is a reverse PCR primer for amplifying SEQ ID NO: 81.

SEQ ID NO: 87 is a forward PCR primer for amplifying SEQ ID NO: 82.

SEQ ID NO: 88 is a reverse PCR primer for amplifying SEQ ID NO: 82.

SEQ ID NO: 89 is a forward PCR primer for amplifying SEQ ID NO: 83.

SEQ ID NO: 90 is a reverse PCR primer for amplifying SEQ ID NO: 83.

SEQ ID NO: 91 is a forward PCR primer for amplifying SEQ ID NO: 84.

SEQ ID NO: 92 is a reverse PCR primer for amplifying SEQ ID NO: 84.

SEQ ID NO: 93 is a probe for detecting the PRR resistance locus of SEQ ID NO: 81.

SEQ ID NO: 94 is a second probe for detecting the PRR resistance locus of SEQ ID NO: 81.

SEQ ID NO: 95 is a probe for detecting the PRR resistance locus of SEQ ID NO: 82.

SEQ ID NO: 96 is a second probe for detecting the PRR resistance locus of SEQ ID NO: 82.

SEQ ID NO: 97 is a probe for detecting the PRR resistance locus of SEQ ID NO: 83.

SEQ ID NO: 98 is a second probe for detecting the PRR resistance locus of SEQ ID NO: 83.

SEQ ID NO: 99 is a probe for detecting the PRR resistance locus of SEQ ID NO: 84.

SEQ ID NO: 100 is a second probe for detecting the PRR resistance locus of SEQ ID NO: 84.

SEQ ID NO: 101 is a third probe for detecting the PRR resistance locus of SEQ ID NO: 8.

SEQ ID NO: 102 is a fourth probe for detecting the PRR resistance locus of SEQ ID NO: 8.

SEQ ID NO: 103 is a third probe for detecting the PRR resistance locus of SEQ ID NO: 10.

SEQ ID NO: 104 is a fourth probe for detecting the PRR resistance locus of SEQ ID NO: 10.

SEQ ID NO: 105 is a third probe for detecting the PRR resistance loci of SEQ ID NO: 14.

SEQ ID NO: 106 is a fourth probe for detecting the PRR resistance loci of SEQ ID NO: 14.

SEQ ID NO: 107 is a third probe for detecting the PRR resistance loci of SEQ ID NO: 15.

SEQ ID NO: 108 is a fourth probe for detecting the PRR resistance loci of SEQ ID NO: 15.

SEQ ID NO: 109 is a fifth probe for detecting the PRR resistance locus of SEQ ID NO: 8.

SEQ ID NO: 110 is a sixth probe for detecting the PRR resistance locus of SEQ ID NO: 8.

SEQ ID NO: 111 is a fifth probe for detecting the PRR resistance locus of SEQ ID NO: 10.

SEQ ID NO: 112 is a sixth probe for detecting the PRR resistance locus of SEQ ID NO: 10.

SEQ ID NO: 113 is a fifth probe for detecting the PRR resistance loci of SEQ ID NO: 14.

SEQ ID NO: 114 is a sixth probe for detecting the PRR resistance loci of SEQ ID NO: 14.

SEQ ID NO: 115 is a fifth probe for detecting the PRR resistance locus of SEQ ID NO: 15.

SEQ ID NO: 116 is a sixth probe for detecting the PRR resistance locus of SEQ ID NO: 15.

DETAILED DESCRIPTION OF THE INVENTION

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 3$^{rd}$ Edition, Garland Publishing, Inc.: New York, 1994; Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 CFR §1.822 is used.

An "allele" refers to an alternative sequence at a particular locus; the length of an allele can be as small as 1 nucleotide base, but is typically larger.

A "locus" is a position on a genomic sequence that is usually found by a point of reference; e.g., a short DNA sequence that is a gene, or part of a gene or intergenic region. The loci of this invention comprise one or more polymorphisms in a population; i.e., alternative alleles present in some individuals.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, "marker" means a polymorphic nucleic acid sequence or nucleic acid feature. A marker may be represented by one or more particular variant sequences, or by a consensus sequence. In another sense, a "marker" is an isolated variant or consensus of such a sequence. In a broader aspect, a "marker" can be a detectable characteristic that can be used to discriminate between heritable differences between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "typing" refers to any method whereby the specific allelic form of a given soybean genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the term "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein said polymorphism constitutes a single base pair change, an insertion of one or more base pairs, or a deletion of one or more base pairs.

As used herein, the term "haplotype" means a chromosomal region within a haplotype window defined by at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, "resistance allele" means the isolated nucleic acid sequence that includes the polymorphic allele associated with resistance to PRR.

As used herein, the term "soybean" means *Glycine max* and includes all plant varieties that can be bred with soybean, including wild soybean species.

As used herein, the term "comprising" means "including but not limited to".

As used herein, the term "elite line" means any line that has resulted from breeding and selection for superior agronomic performance. An elite plant is any plant from an elite line. Non-limiting examples of elite soybean varieties that are commercially available to farmers or soybean breeders include AG00802, A0868, AG0902, A1923, AG2403, A2824, A3704, A4324, A5404, AG5903 and AG6202 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); and DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS13-K2 (NK Division of Syngenta Seeds, Golden Valley, Minn., USA); 90M01, 91M30, 92M33, 93M11, 94M30, 95M30 and 97B52 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-B1, S53-A1, S76-L9 and S78-G6 (Syngenta Seeds, Henderson, Ky., USA). An elite plant is a representative plant from an elite variety.

The present invention provides SNP genetic markers useful for screening and selecting for PRR resistance at the Rps1 locus located on Linkage Group N (LG N) (Cregan, et al. *Crop Sci.* 39:1464-1490 (1999)). The present invention also provides SNP DNA markers useful for screening and selecting for PRR resistance at the Rps3 locus located on Linkage Group F (LG F) and the Rps8 locus located on Linkage Group F (LG F) (Cregan, et al. *Crop Sci.* 39:1464-1490 (1999)). The SNP markers are useful for monitoring the selection for and introgression of the PRR resistance loci from PRR resistant sources. As used herein, the Rps1 locus includes, for example, Rps1a, Rps1b, Rps1c, Rps1d, and Rps1k. Further, as used herein, the Rps3 locus includes, for example, Rps3a, Rps3b, and Rps3c.

The present invention also includes a method of selecting or introgressing a PRR resistant allele into a soybean plant comprising: (A) crossing at least one PRR resistant soybean plant with at least one other soybean plant in order to form a population;
(B) screening the population with one or more nucleic acid markers to determine if one or more soybean plants from the population contains the allele of the PRR resistance source.

SNP markers used to monitor the selection or introgression of the PRR resistance locus 1 (Rps1) include those selected from the group consisting of NS0099413, NS0102174, NS0118166, NS0102920, NS0114258, NS0118976, NS0119981, NS0119335, NS0201536, NS0138011, NS0202603, NS0203225, NS0129030, and NS0127084. Sources of Rps1 include both accession germplasm, such as plant introductions, and elite germplasm. Sources include, but are not limited to, Williams 82, L75-3735, and elite varieties with demonstrated PRR resistance. PRR resistance SNP marker DNA sequences (SEQ ID NO: 1 through 10 and SEQ ID NO: 81 through 84) can be amplified using the primers indicated as SEQ ID NO: 17 through 36 and SEQ ID NO: 85 through 92 and detected with probes indicated as SEQ ID NO: 49 through 68 and SEQ ID NO: 93 through 100, wherein the corresponding primer and probe sets provide assays for the detection of PRR resistance or susceptibility in *Glycine max*. Determination of resistance or susceptibility of a plant to a particular pathogen is obvious to anyone skilled in the art.

In the present invention, a PRR resistance locus 3 (Rps3) is located on Linkage Group F (Cregan, et al. *Crop Sci.* 39:1464-1490 (1999)). SNP markers used to monitor the introgression of Rps3 can be selected from the group consisting of NS0114683, NS0101324, NS0102483, NS0119333, NS0102262, and NS0116265. Sources of Rps3 include both accession and elite germplasm. Sources of Rps3 include, but are not limited to, L83-570, L89-1541, L92-7857, Ivory, and elite varieties with demonstrated PRR resistance. In the present invention, a PRR resistance locus 8 (Rps8) is located on Linkage Group F (Cregan, et al. *Crop Sci.* 39:1464-1490 (1999)). SNP markers used to monitor the introgression of PRR resistance locus 8 can be selected from the group consisting of NS0114683, NS0101324, NS0102483, NS0119333, NS0102262, and NS0116265. Sources of Rps8 include accession germplasm. Sources of Rps8 include, but are not limited to, PI399703 and other varieties with known PRR resistance.

In one aspect, the present invention provides methods and compositions for screening soybean plants for resistance or susceptibility to PRR, caused by the species *Phytophthora sojae*. In another aspect, the present invention provides methods and compositions for selecting PRR resistant plants. In a preferred aspect, the present invention provides methods and compositions for selecting for and introgressing PRR resistance into soybean plants. The PRR resistance alleles of the present invention may be introduced into an elite *Glycine max* line.

As used herein, PRR refers to any PRR race, variant or isolate. A soybean plant of the present invention can be resistant to one or more oomycete capable of causing or inducing PRR. In one aspect, the present invention provides plants resistant to and methods and compositions for screening soybean plants for resistance or susceptibility to *Phytophthora sojae* races 1 through 55. In another aspect, the present invention provides plants resistant to and methods and compositions for screening soybean plants for resistance or susceptibility to *Phytophthora sojae* race 1. In additional aspect, the present invention provides plants resistant to and methods and compositions for screening soybean plants for resistance or susceptibility to *Phytophthora sojae* race 3. In a further aspect, the present invention provides plants resistant to and methods and compositions for screening soybean plants for resistance or susceptibility to *Phytophthora sojae* race 4. The invention further provides plants resistant to and methods and compositions for screening soybean plants for resistance or susceptibility to *Phytophthora sojae* race 7. The invention further provides plants resistant to and methods and compositions for screening soybean plants for resistance or susceptibility to *Phytophthora sojae* race 17. The invention further provides plants resistant to and methods and compositions for screening soybean plants for resistance or susceptibility to *Phytophthora sojae* race 25.

The PRR resistance alleles of the present invention may also be introduced into an elite *Glycine max* transgenic plant that contains one or more genes for herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistance, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in *Glycine max*.

A disease resistance allele or alleles can be introduced from any plant that contains that allele (donor) to any recipient soybean plant. In one aspect, the recipient soybean plant can contain additional PRR resistance loci. In another aspect, the recipient soybean plant can contain a transgene. In another aspect, while maintaining the introduced PRR resistance allele, the genetic contribution of the plant providing the disease resistance allele can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the PRR resistance locus or loci of interest.

It is further understood that a soybean plant of the present invention may exhibit the characteristics of any relative maturity group. In an aspect, the maturity group is selected from the group consisting of 000, 00, 0, 1, 2, 3, 4, 5, 6, 7, 8, 9, and 10.

The present invention also provides for parts of the plants of the present invention. Plant parts, without limitation, include seed, endosperm, ovule and pollen. In a particularly preferred aspect of the present invention, the plant part is a seed.

Plants or parts thereof of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., Plant Science Letters, 19: 193-201 (1980); Cheng et al., *Plant Science Letters,* 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

Plants containing one or more PRR resistance loci described can be donor plants. Soybean plants containing resistance loci can be, for example, screened for by using a nucleic acid molecule capable of detecting a marker polymorphism associated or genetically linked with each of the resistance alleles.

As used herein, an allele of a disease resistance locus can encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the resistance allele comprises one or more genes or other genetic factors that are also capable of exhibiting allelic variation. The use of the term "a resistance allele" does not exclude a genomic region that comprises more than one gene or other genetic factor. Specifically, a "disease resistance allele" in the present in the invention can denote a haplotype allele within a haplotype window or genomic region wherein a phenotype associated with said halplotype allele can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular PRR resistance locus or for a particular polymorphic marker.

The present invention includes isolated nucleic acid molecules. Such molecules include those nucleic acid molecules capable of detecting a polymorphism genetically or physically linked to a PRR resistance locus. Additional markers can be obtained that are genetically linked to Rps1, Rps3, and Rps8, by available techniques. In one aspect, the nucleic acid molecule is capable of detecting the presence or absence of a marker located less than 30, 25, 20, 10, 5, 2, or 1 centimorgans from a PRR resistance locus. In another aspect, the nucleic acid molecule is capable of detecting a marker in a locus selected from the group Rps1, Rps3, and Rps8. In a further aspect, a nucleic acid molecule is selected from the group consisting of SEQ ID NO: 1 to SEQ ID NO: 116, fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NO: 1 through SEQ ID NO: 116 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NO: 1 through SEQ ID NO: 116 or complements or fragments of either under high stringency conditions. In one aspect of the present invention, a preferred marker nucleic acid molecule of the present invention has the nucleic acid sequence set forth in SEQ ID NO: 1 through SEQ ID NO: 116 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 1 through SEQ ID NO: 116 or complement thereof or fragments of either. In a further aspect of the present invention, a preferred marker nucleic acid molecule of the present invention shares between 95% and 100% sequence identity with the sequence set forth in SEQ ID NO: 1 through SEQ ID NO: 116 or complement thereof or fragments of either. In a more preferred aspect of the present invention, a preferred marker nucleic acid molecule of the present invention shares between 98% and 100% sequence identity with the nucleic acid sequence set forth in SEQ ID NO: 1 through SEQ ID NO: 116 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual, 2nd Edition, Cold Spring Harbor Press*, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 *Nucl. Acids Res.* 12:203-213; and Wetmur et al. 1968 *J. Mol. Biol.* 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 1 to SEQ ID NO: 116 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100. In another aspect, the fragment can be greater than 10, 15, 20, 25, 30, 35, 40, 50, 100, or 250 nucleotides.

Additional genetic markers can be used to select plants with an allele of a QTL associated with disease resistance of soybean of the present invention. Examples of public marker databases include, for example, Soybase, an Agricultural Research Service, United States Department of Agriculture.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers, such as single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with alleles of a QTL of the present invention can be utilized.

In one embodiment, nucleic acid-based analyses for the presence or absence of the genetic polymorphism can be used for the selection of seeds in a breeding population. A wide variety of genetic markers for the analysis of genetic polymorphisms are available and known to those of skill in the art. The analysis may be used to select for genes, QTL, alleles, or genomic regions (haplotypes) that comprise or are linked to a genetic marker.

Herein, nucleic acid analysis methods are known in the art and include, but are not limited to, PCR-based detection methods (for example, TaqMan assays), microarray methods, and nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. Cold Spring Harbor Symp. Quant. Biol. 51:263-273 (1986); European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in soybean genomic DNA samples. These soybean genomic DNA samples used include but are not limited to soybean genomic DNA isolated directly from a soybean plant, cloned soybean genomic DNA, or amplified soybean genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464 employing at least one pair of probes having sequences homologous to adjacent portions of the target nucleic acid sequence and having side chains which non-covalently bind to form a stem upon base pairing of said probes to said target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of soybean genomic DNA which flanks a region containing the polymorphism to be assayed. Following amplification of the region of the soybean genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In a preferred method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3'quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

For the purpose of QTL mapping, the markers included should be diagnostic of origin in order for inferences to be made about subsequent populations. SNP markers are ideal for mapping because the likelihood that a particular SNP allele is derived from independent origins in the extant populations of a particular species is low, particularly if multiple SNPs are used in tandem to define a haplotype. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al. (Lander et al., Genetics, 121:185-199 (1989)), and the interval mapping, based on maximum likelihood methods described therein, and implemented in the software package MAPMAKER/QTL (Lincoln and Lander, Mapping Genes Controlling Quantitative Traits Using MAPMAKER/QTL, Whitehead Institute for Biomedical Research, Mass., (1990)). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arus and Moreno-González, Plant Breeding, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al., Genetics, 139:1421-1428 (1995)). Multiple regression methods or models can be also be used, in which the trait is regressed on a large number of markers (Jansen Biometrics in Plant Breed, van Oijen, Jansen (eds.) Proceedings of the Ninth Meeting of the Eucarpia Section Biometrics in Plant Breeding, The Netherlands, pp. 116-124 (1994); Weber and Wricke, Advances in Plant Breeding, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al., Genetics, 136:1447-1455 (1994)) and Zeng (Zeng, Genetics 136: 1457-1468 (1994)). Generally, the use of cofactors reduces the bias and sampling error of the estimated QTL positions (Utz and Melchinger, Biometrics in Plant Breeding, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al., Theor. Appl. Genet. 91:33-3 (1995)).

Selection of appropriate mapping populations is important to map construction. The choice of an appropriate mapping population depends on the type of marker systems employed (Tanksley et al., Molecular mapping in plant chromosomes. chromosome structure and function: Impact of new concepts J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., Proc. Natl. Acad. Sci. (USA) 89:1477-1481 (1992)). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al. (1992)). Information obtained from backcross populations analyzed using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al. 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pure line cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivar can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, *Plant breeding perspectives*, Wageningen (ed), Center for Agricultural Publishing and Documentation (1979); Fehr, *In: Soybeans: Improvement, Production and Uses*, 2nd Edition, Manograph., 16:249 (1987); Fehr, "Principles of variety development," *Theory and Technique*, (Vol. 1) and Crop Species Soybean (Vol. 2), Iowa State Univ., Macmillan Pub. Co., NY, 360-376 (1987).

An alternative to traditional QTL mapping involves achieving higher resolution by mapping haplotypes, versus individual markers (Fan et al. 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

It is further understood, that the present invention provides bacterial, viral, microbial, insect, mammalian and plant cells comprising the nucleic acid molecules of the present invention.

As used herein, a "nucleic acid molecule," be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al., *Science* 238:336-340 (1987); Albarella et al., European Patent 144914), chemical labels (Sheldon et al., U.S. Pat. No. 4,582,789; Albarella et al., U.S. Pat. No. 4,563, 417), modified bases (Miyoshi et al., European Patent 119448).

Apparatus and methods for the high-throughput, non-destructive sampling of seeds have been described which would overcome the obstacles of statistical samples by allowing for individual seed analysis. For example, U.S. patent application Ser. No. 11/213,435 (filed Aug. 26, 2005) and U.S. patent application Ser. No. 11/680,611 (filed Mar. 2, 2007), which are incorporated herein by reference in their entirety, disclose apparatus and systems for the automated sampling of seeds as well as methods of sampling, testing and bulking seeds.

The disease resistant effect of the QTL can vary based on the parental genotype and on the environmental conditions in which the disease resistance effect is measured. It is within the skill of those in the art of plant breeding and without undue experimentation to use the methods described herein to select from a population of plants or from a collection of parental genotypes those that when containing a disease locus result in enhanced disease resistance relative to the parent genotype.

Having now generally described the invention, the same will be more readily understood through reference to the following examples which are provided by way of illustration, and are not intended to be limiting of the present invention, unless specified.

EXAMPLES

Example 1

Validation of SNP Markers for Introgression of PRR Resistance Loci when Used in Conjunction with Haplotype of Known Resistance Source

*Phytophthora sojae* is the causal agent of *Phytophthora* root rot (PRR) and accounts for significant soybean yield loss in the United States. Planting resistant varieties is an effective method of controlling PRR. Breeding for PRR resistant soybeans can be greatly facilitated by the use of marker-assisted selection for PRR resistance alleles. Segregating populations were generated to validate SNP markers that could be used to detect, select for, and introgress PRR resistance loci into plants The phenotypic rating scale and definitions used herein for the following Examples are included in Table 1. The percentage of plants surviving after inoculation with *P. sojae* is used for classification. This rating scale provides the basis for all disease ratings and determinations of resistance or susceptibility in the following Examples.

TABLE 1

Description of rating criteria used for PRR phenotyping.

| Phenotypic Results | Rating |
|---|---|
| 0-25% Dead | Resistant (R) |
| 26-49% Dead | Heterozygous (H) |
| ≥50% Dead | Susceptible (S) |

Segregating populations, involving crosses between a susceptible cultivar and a series of isolines containing Rps resistance alleles, were developed for genetic mapping in the summer of 2004 (Table 2). Individual F2 plants were tissue sampled and screened with markers polymorphic for the Rps resistant locus associated with the resistance source. F2:3 seed of the harvested F2 plants was analyzed for the PRR reaction. Results from validation experiments demonstrating of the utility of the markers are provided in Tables 3 through 10.

TABLE 2

Screening Populations for the PRR reaction

| Resistant Parent | Resistant locus | Susceptible Parent |
|---|---|---|
| L75-3735 | Rps1c | MV0030 |
| Williams 82 | Rps1k | MV0030 |
| L83-570 | Rps3a | MV0030 |
| L89-1541 | Rps3b | MV0030 |
| L92-7857 | Rps3c | MV0030 |
| PI399703 | Rps8 | Williams |

L75-3735 is a known source of Rps1c. From the L75-3735/MV0030 population, a total of 322 F2 pants were tissue sampled for marker screening. The seed harvested from each plant was used to plant and phenotype individual F3 plants from each F2-derived family for reaction to PRR. Plants exhibiting a resistant reaction were found to have a different haplotype from that of susceptible plants when screened with genetic markers NS0102174, NS0118976, NS0118166, NS0099413, and NS0119335. The total number of families from the L75-3735/MV0030 population with the same haplotype as the resistant parent was 41, and of these families, all 41 had a resistant reaction when phenotyped. From each family, an average of 10 F2 derived F3 plants (F2 families) were phenotyped. Table 3 provides an example of the PRR reaction and haplotype of two families from the L75-3735/MV0030 population.

TABLE 3

Validation of SNP markers used in conjunction with the haplotype of a known Rps1c source.

| Family | Total Plants | Susc. Plants | Reaction | Pedigree | NS-0102174 | NS-0118976 | NS-0118166 | NS-0099413 | NS-0119335 |
|---|---|---|---|---|---|---|---|---|---|
| 1 | 12 | 0 | R | L75-3735/MV0030 | GG | TT | TT | CC | TT |
| 2 | 11 | 10 | S | L75-3735/MV0030 | CC | CC | CC | TT | AA |

Williams 82 is a known source of Rps1k. From the Williams82/MV0030 population, a total of 205 F2 plants were tissue sampled for marker screening. The seed harvested from each plant was used to plant and phenotype individual F3 plants from each F2-derived family for reaction to PRR. Plants exhibiting a resistant reaction were found to have a different haplotype from that of susceptible plants when screened with genetic markers NS0118166, NS0102920, NS0114258, NS0102174, NS0119981, and NS0201536. The total number of families from the Williams 82/MV0030 population with the same haplotype as the resistant parent was 24, and of these families, all 24 had a resistant reaction when phenotyped. Table 4 provides an example of the PRR reaction and haplotype of two families from the Williams82/MV0030 population.

TABLE 4

Validation of SNP markers used in conjunction with the haplotype of a known Rps1k source.

| Family | Total Plants | Susc. Plants | Reaction | Pedigree | NS-0118166 | NS-0102920 | NS-0114258 | NS-0118976 | NS-0102174 | NS-0119981 | NS-0201536 |
|---|---|---|---|---|---|---|---|---|---|---|---|
| 1 | 12 | 0 | R | Williams82/MV0030 | TT | CC | TT | TT | GG | CC | CGAG |
| 2 | 10 | 10 | S | Williams82/MV0030 | CC | TT | CC | CC | CC | AA | **** |

("*" indicates a single nucleotide deletion)

L83-570 is a known source of Rps3a. From the L83-570/MV0030 population, a total of 297 F2 plants were tissue sampled for marker screening. The seed harvested from each plant was used to plant and phenotype individual F3 plants from each F2-derived family for reaction to PRR. Plants exhibiting a resistant reaction were found to have a different haplotype than susceptible plants when screened with the genetic markers NS0101324 and NS0116265. The total number of families from the L83-570/MV0030 population with the same haplotype as the resistant parent was 64, and of these families, 58 were found to have a resistant reaction when phenotyped. Table 5 provides an example of the PRR reaction and haplotype for two families from the L83-570/MV0030 population.

TABLE 5

Validation of SNP markers used in conjunction with haplotype of a known Rps3a source.

| Family | Total Plants | Susc. Plants | Reaction | Pedigree | NS-0101324 | NS-0116265 |
|---|---|---|---|---|---|---|
| 1 | 11 | 0 | R | L83-570/MV0030 | AA | GG |
| 2 | 10 | 9 | S | L83-570/MV0030 | GG | TT |

L89-1541 is a known source of Rps3b. From the L89-1541/MV0030 population, a total of 345 F2 plants were tissue sampled for marker screening. The seed harvested from each plant was used to plant and phenotype individual F3 plants from each F2-derived family for reaction to PRR. Plants exhibiting a resistant reaction were found to have a different haplotype than susceptible plants when screened with the genetic markers NS0114683, NS0102483, NS0119333, and NS0102262. The total number of families from the L89-1541/MV0030 population with the same haplotype of the resistant parent was 88, and of these families, 47 were found to have a resistant reaction when phenotyped. Table 6 provides an example of the PRR reaction and haplotype of two families from the L89-1541/MV0030 population.

TABLE 6

Validation of SNP markers used in conjunction with haplotype of known source of Rps3b.

| Family | Total Plants | Susc. Plants | Reaction | Pedigree | NS-0114683 | NS-0102483 | NS-0119333 | NS-0102262 |
|---|---|---|---|---|---|---|---|---|
| 1 | 12 | 0 | R | L89-1541/MV0030 | AA | GG | AA | AA |
| 2 | 12 | 12 | S | L89-1541/MV0030 | CC | AA | CC | GG |

L92-7857 is a known or Rps3c. From the L92-7857/MV0030 population, a total of 340 F2 plants were tissue sampled for marker screening. The seed harvested from each plant was used to plant and phenotype individual F3 plants from each F2-derived family for reaction to PRR. Plants exhibiting a resistant reaction were found to have a different haplotype than susceptible plants when screened with genetic markers NS0114683, NS0102483, NS0119333, and NS0102262. The total number of families from the L92-7857/MV0030 population with the same haplotype of the resistant parent was 112, and of these families, 87 were found to have a resistant reaction when phenotyped. Table 7 provides an example of the PRR reaction and haplotype of two of the families from the L92-7857/MV0030 population.

TABLE 7

Validation of SNP markers used in conjunction with the haplotype of a known source of Rps3c.

| Family | Total Plants | Susc. Plants | Reaction | Pedigree | NS-0114683 | NS-0102483 | NS-0119333 | NS-0102262 |
|---|---|---|---|---|---|---|---|---|
| 1 | 11 | 0 | R | L92-7857/MV0030 | AA | GG | AA | AA |
| 2 | 12 | 11 | S | L92-7857/MV0030 | AC | AG | AC | AG |

PI399703 is a known source of Rps8. From the PI399703/Williams population, a total of 223 F2 plants were tissue samples for marker screening. The seed harvested from each plant was used to plant and phenotype individual F3 plants from each F2-derived family for reaction to PRR. Plants exhibiting a resistant reaction were found to have a different haplotype than susceptible plants when screened with genetic markers NS0114683, NS0102483, NS011933, and NS0102262. The total number of families from the PI399703/Williams population with the same haplotype of the resistant parent was 39, and of these families, all 39 had a resistant reaction when phenotyped. Table 8 provides an example of the PRR reaction and haplotype of two families from the PI399703/Williams population.

TABLE 8

Validation of SNP markers used in conjunction with the haplotype of a known source of Rps8.

| Family | Total Plants | Susc. Plants | Reaction | Pedigree | NS-0101324 | NS-0102262 | NS-0102483 | NS-0114683 | NS-0116265 | NS-0119333 |
|---|---|---|---|---|---|---|---|---|---|---|
| 1 | 6 | 0 | R | PI399703/Williams | AA | GG | AA | CC | GG | CC |
| 2 | 4 | 4 | S | PI399703/Williams | GG | AA | GG | AA | TT | AA |

An additional SNP marker, NS0138011, was identified for the detection of the Rps1c locus. Genotyping results of 100 soybean lines which were known to have either Rps1a, Rps1k, Rps1c, or to be susceptible to PRR were examined. Lines with Rps1c were found to have the AA allele when screened with the marker NS0138011. The other 85 lines, which had either PRR resistance loci Rps1a, Rps1k, or were susceptible to PRR, had the CC allele as provided in Table 9. Therefore, screening with the genetic marker NS0138011 can be used for detecting the Rps1c locus in a soybean breeding program.

TABLE 9

Validation of SNP marker NS0138011 in detecting Rps1c.

| Allele | Number of lines | Locus |
|---|---|---|
| CC | 85 | Rps1a, Rps1k or susceptible |
| AA | 15 | Rps1c |

Table 10 summarizes validation experiments and includes the SNP markers found to be useful in monitoring the selection or introgression of the PRR resistance locus Rps1, including Rps1c and Rps1k alleles into a soybean plant in a soybean breeding program. The haploype of the known resistance source is used to determine which Rps1 allele is selected for in a breeding program. Table 10 also includes SNP markers useful for monitoring the introgression of the PRR resistance loci Rps3 and Rps8 into a soybean plant in a soybean breeding program. PRR resistance locus Rps3 includes, Rps3a, Rps3b, and Rps3c. The haplotype of the known resistance source is used to determine which Rps3 allele is selected for in a breeding program. SNP markers found to be useful for screening for Rps1 include NS0099413, NS0102174, NS0118166, NS0102920, NS0114258, NS0118976, NS0119981, NS0119335, NS0201536, NS0138011, NS0127084, NS0129030, NS0202603, and NS0203225. SNP markers found to be useful for screening for Rps3 and Rps8 include NS0114683, NS010324, NS0102483, NS0119333, NS0102262, and NS0116265. In a soybean breeding program, plants genotyped as homozygous or heterozygous for the resistant parent alleles, may be selected for advancement.

TABLE 10

SNP markers useful for introgression of PRR resistance loci Rps1, Rps3, and Rps8 into soybean plants when used in conjunction with the known haplotype of the resistance source.

| Marker | LG* | Chr. Pos. | Rps Locus | SEQ ID | SNP Position | Allele 1 | Allele 2 | SEQ ID Forward Primer | SEQ ID Reverse Primer | SEQ ID Probe 1 | SEQ ID Probe 2 |
|---|---|---|---|---|---|---|---|---|---|---|---|
| NS0099413 | N | 25.0 | 1 | 1 | 242 | CC | TT | 17 | 18 | 49 | 50 |
| NS0102174 | N | 25.0 | 1 | 2 | 563 | CC | GG | 19 | 20 | 51 | 52 |

TABLE 10-continued

SNP markers useful for introgression of PRR resistance loci Rps1, Rps3, and Rps8 into soybean plants when used in conjunction with the known haplotype of the resistance source.

| Marker | LG* | Chr. Pos. | Rps Locus | SEQ ID | SNP Position | Allele 1 | Allele 2 | SEQ ID Forward Primer | SEQ ID Reverse Primer | SEQ ID Probe 1 | SEQ ID Probe 2 |
|---|---|---|---|---|---|---|---|---|---|---|---|
| NS0118166 | N | 25.0 | 1 | 3 | 259 | CC | TT | 21 | 22 | 53 | 54 |
| NS0102920 | N | 25.0 | 1 | 4 | 163 | CC | TT | 23 | 24 | 55 | 56 |
| NS0114258 | N | 25.0 | 1 | 5 | 324 | CC | TT | 25 | 26 | 57 | 58 |
| NS0118976 | N | 25.0 | 1 | 6 | 460 | CC | TT | 27 | 28 | 59 | 60 |
| NS0119981 | N | 28.7 | 1 | 7 | 516 | AA | CC | 29 | 30 | 61 | 62 |
| NS0119335 | N | 29.5 | 1 | 8 | 310 | AA | TT | 31 | 32 | 63 | 64 |
| NS0202603 | N | 31.1 | 1 | 81 | 51 | AA | GG | 85 | 86 | 93 | 94 |
| NS0138011 | N | 32.2 | 1 | 10 | 385 | AA | CC | 35 | 36 | 67 | 68 |
| NS0201536 | N | 33.0 | 1 | 9 | 35-38 | CGAG | **** | 33 | 34 | 65 | 66 |
| NS0203225 | N | 33.2 | 1 | 82 | 192 | AA | TT | 87 | 88 | 95 | 96 |
| NS0129030 | N | 34.7 | 1 | 83 | 324 | CC | AA | 89 | 90 | 97 | 98 |
| NS0127084 | N | 41.4 | 1 | 84 | 858 | CC | TT | 91 | 92 | 99 | 100 |
| NS0114683 | F | 100.6 | 3.8 | 11 | 368 | AA | CC | 37 | 38 | 69 | 70 |
| NS0101324 | F | 100.8 | 3.8 | 12 | 84 | AA | GG | 39 | 40 | 71 | 72 |
| NS0102483 | F | 101.7 | 3.8 | 13 | 172 | AA | GG | 41 | 42 | 73 | 74 |
| NS0119333 | F | 101.7 | 3.8 | 14 | 607 | AA | CC | 43 | 44 | 75 | 76 |
| NS0102262 | F | 103.0 | 3.8 | 15 | 131 | AA | GG | 45 | 46 | 77 | 78 |
| NS0116265 | F | 113.8 | 3.8 | 16 | 719 | GG | TT | 47 | 48 | 79 | 80 |

*LG = Linkage Group

Example 2

Use of SNP Markers to Select for the Rps1k Locus Which Confers Resistance to PRR Race 4

SNP markers were used with knowledge of PRR resistant germplasm to breed for PRR resistance (Table 11). The F3 population derived from the cross of two PPR resistance sources AG3602, a source of Rps1c, and AG3505, a source of Rps1k, was screened with two SNP markers. A total of 466 individuals were screened. The SNP markers NS0119335 and NS0118166 were used to select for Rps1k based on the haplotype of AG3505, a source of resistance for PRR race 4.

Sources of Rps1 resistance include, but are not limited to AG3602, AG3505, and DKB28-53.

TABLE 11

Haplotypes of two sources of PRR resistance.

|  | Marker 1 | Marker 2 |
|---|---|---|
| Source | NS0119335 | NS0118166 |
| AG3602 (Rps1c) | TT | CC |
| AG3505 (Rps1k) | AA | TT |

Example 3

Use of SNP Markers to Monitor the Introgression of PRR Resistance Locus Rps1k F3 individuals derived from a cross between two soybean lines AG3602 (Rps1c) and AG3505 (Rps1k) were genotyped. The Rps1k locus provides resistance to PRR race 4. A total of 466 F3 plants are screened with two SNP markers NS0119335 and NS0118160. Table 12 reports the results of the phenotypic validation of the genotypic screening for PRR race 4. Screening with NS0119335 was 85.7% predictive of PRR reaction. Screening with NS0118160 was 83.8% predictive of PRR reaction.

TABLE 12

Results from phenotypic screening following selection based on resistance source haplotype.

| Marker | Favorable Haplotype | Individuals selected based on haplotype | Individuals with Res. Reaction | % Resistant | Origin |
|---|---|---|---|---|---|
| NS0119335 | AA | 182 | 156 | 85.7 | AG3602/AG3505 |
| NS0118160 | TT | 185 | 155 | 83.8 | AG3602/AG3505 |

Example 4

Use of SNP Markers to Select for Rps3 or Rps8 Which Confer Resistance to PRR Race 25

F3 plants derived from the following breeding populations were genotyped with the SNP marker NS0114683. Rps3 and Rps8 provide resistance to PRR race 25. The breeding populations included a source of either Rps3 or Rps8. Table 13 reports the results of the phenotypic validation of the genotypic screening for PRR race 25. Screening with NS0114683 for Rps3 was 96.4 to 100% predictive of the PRR reaction. Screening with NS0114683 for Rps8 was 72.4 to 80.8% predictive of the PRR reaction.

TABLE 13

SNP marker NS-0114683 was used to select plants with haplotype matching resistance source. Phenotypic screening with PRR race 25 was then conducted.

| Favorable Haplotype | Individuals selected based on haplotype | Individuals with Res. Reaction | % Resistant | Rps | Origin |
|---|---|---|---|---|---|
| CC | 17 | 17 | 100.0 | Rps3 | Ivory/DKB28-53 |
| CC | 48 | 47 | 97.9 | Rps3 | MV0033/CFN3303E3R |
| CC | 28 | 27 | 96.4 | Rps3 | Ivory/MV0036 |
| CC | 26 | 21 | 80.8 | Rps8 | DKB28-53/((Darby/OX-98317)/AG2703)) |
| CC | 29 | 21 | 72.4 | Rps8 | MV0039/((Darby/OX-98317)/MV0028)) |

Example 5

Introgression of Race Specific PRR Resistance Using SNP Markers

In this example, L75-3735 was the source of PRR resistance locus Rps1c. Populations from a cross of L75-3735 with MV0030, a line susceptible to PRR race 3, were analyzed. Two markers, NS0099413 and NS0119335, were used to select individuals with haplotypes matching that of the resistant parent. Individuals homozygous for the alleles present in the PRR resistant source (L75-3735) were chosen for advancement (Table 14).

TABLE 14

Use of two SNP markers to screen for resistance or susceptibility to PRR race 3.

| Pedigree | # Dead | Total | % Susc. | Reaction | NS0099413 | NS0119335 |
|---|---|---|---|---|---|---|
| L75-3735 (Rps1c) | 0 | 11 | 0 | R | CC | TT |
| MV0030 | 9 | 10 | 90 | S | TT | AA |
| MV0030 | 5 | 10 | 50 | S | TT | AA |
| L75-3735/MV0030 | 0 | 10 | 0 | R | CC | TT |
| L75-3735/MV0030 | 10 | 10 | 100 | S | TT | AA |
| L75-3735/MV0030 | 5 | 10 | 50 | S | CT | AT |
| L75-3735/MV0030 | 4 | 10 | 40 | H | CT | AT |

Example 6

Use of SNP Markers to Select for PRR Resistance

Further SNP markers were identified which flanked marker NS0138011. The alleles of NS0138011 have been associated with Rps1c. The "A" allele has been shown to indicate the presence of Rps1c and the "C" allele indicates the absence of Rps1c. The combination of markers NS0202603, NS0138011, and NS0203225 demonstrate utility for distinguishing multiple alleles at the Rps1 locus including rps (susceptible), Rps1a, Rps1c, and Rps1k. In a study of 239 soybean lines, the haplotypes of three markers were effective in predicting the PRR reaction from 88 to 100% of the time (Table 15). In a soybean breeding program, the three markers can be used to identify plants with resistance to Rps1a, Rps1c, and Rps1k, thus allowing for marker assisted selection.

TABLE 15

Ability of marker haplotypes of NS0202603, NS0138011, and NS0203225 to predict allele configuration of Rps1 for PRR resistance.

| Predicted Rps1 allele | Haplotype NS0202603-NS0138011-NS0203225 | # lines with haplotype | # lines that show phenotype of predicted allele* | % congruence |
|---|---|---|---|---|
| rps | GG CC AA | 9 | 9 | 100 |
| Rps1a | AA CC TT | 9 | 8 | 89 |
| Rps1c | AA AA AA | 189 | 186 | 98 |
| Rps1k | GG CC TT | 32 | 28* | 88 |

*3 are heterozygous based on phenotype

Example 7

Use of SNP Markers and Knowledge of Parental Genotype to Identify Rps1c Resistant Plants NS0129030 is useful for selecting for the Rps1c allele in populations of late Maturity Group 3 parents that have Rps1c and are crossed to susceptible Maturity Group 4 parents. For example, when AG3802, AG3905, AOX3903B0C, CFN3802A1X, or AG3602 are used as Rps1c donors in crosses to the PRR-susceptible lines MV0097, MV0098, MV0099, or MV0022, all of the resistant parents have the "C" allele at NS0129030, while all of the susceptible parents have the "A" allele. Knowledge of the resistant source genotype is important since the association of the "C" allele with Rps1c is not present in all other lines, as the susceptible lines MV0101, MV0102, and MV0103 also have the "C" allele at this locus. Therefore in a soybean breeding program, the marker NS0129030 can be used with knowledge of the resistant source genotype to select resistant plants.

NS0127084 is also useful in many of the same populations. For example, the Rps1c donors AG3802, AG3905, AOX3903B0C, CFN3802C1X, or AG3602 all have the "C" allele at the NS0127084 locus, while the susceptible lines MV0097, MV0099, and MV0100 all have the "T" allele. However, MV0098 also has the "C" allele, but lacks Rps1c. Therefore in a soybean breeding program, the marker NS0127084 can be used with knowledge of the resistant source genotype to select resistant plants.

Example 8

Use of SNP Markers to Select for Rps3c

A population was provided from the cross of MV0031/BFN3205A0R, with BFN3205A0R as the heterozygous source of Rps3c which confers resistance to *Phytophthora sojae* race 25. The haplotypes of the parents and that of CFN3303E3R, a homozygous sister line of BFN3205A0R, are provided in Table 16. A total of 4,224 F2 seeds were non-destructively sampled and genotyped. Individual seeds were selected which were homozygous favorable for Rps3c. A total of 1018 seeds had the haplotype CCGGGG at the marker loci NS0119333, NS0102262, NS0116265 and were selected for planting. F2 seeds genotyped as homozygous favorable for Rps3c were planted in the Spring of 2006. F2:3 seed from selected plants were planted as progeny rows in 2006-2007. F2:4 seed bulked from selected progeny rows was grown in yield trials in 2007. Four lines selected for superior yield were evaluated for resistance to PRR race 25 to confirm presence of Rps3c. Pathology data are provided in Table 18.

Pathology testing confirmed the marker assisted selection for resistance to *Phytophthora sojae* race 25. From this example, the markers provided have shown use for marker assisted selection for PRR resistance to *Phytophthora sojae* race 25.

TABLE 16

Haplotypes of MV0031, BFN3205A0R, and CFN3303E3R.

| Line | NS0119333 | NS0102262 | NS0116265 |
|---|---|---|---|
| MV0031 | AA | AA | GG |
| BFN3205A0R | AC | AG | TT |
| CFN3303E3R | CC | GG | GG |

TABLE 17

Pathology screening for Rps3 with *Phytophthora sojae* race 25.

| Line | Replications | Total Plants | Susceptible Plants |
|---|---|---|---|
| 1 | 3 | 24 | 0 |
| 2 | 3 | 24 | 0 |
| 3 | 3 | 24 | 0 |
| 4 | 3 | 24 | 0 |

Example 9

Oligonucleotide Hybridization Probes Useful for Detecting Soybean Plants with PRR Resistance Loci Oligonucleotides can also be used to detect or type the polymorphisms associated with PRR resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 18. These oligonucleotides can be detectably labeled with radioactive labels, fluorophores, or other chemiluminescent means to facilitate detection of hybridization to samples of genomic or amplified nucleic acids derived from one or more soybean plants using methods known in the art.

TABLE 18

Oligonucleotide Hybridization Probes*

| Marker | Marker SEQ ID | SNP Position | Hybridization Probe | SEQ ID Probe |
|---|---|---|---|---|
| NS0119335 | 8 | 310 | TCTCAGAGTGGGTAGA | 101 |
| NS0119335 | 8 | 310 | TCTCAGTGTGGGTAGA | 102 |
| NS0138011 | 10 | 385 | GAATGAAAAATCTACT | 103 |
| NS0138011 | 10 | 385 | GAATGACAAATCTACT | 104 |
| NS0119333 | 14 | 607 | TAAGAACCCTCTCCAA | 105 |
| NS0119333 | 14 | 607 | TAAGAAACCTCTCCAA | 106 |
| NS0102262 | 15 | 131 | AAGCCTGACAATTGAT | 107 |
| NS0102262 | 15 | 131 | AAGCCTAACAATTGAT | 108 |

*16mer spanning SNP

Example 10

Oligonucleotide Probes Useful for Detecting Soybean Plants with PRR Resistance Loci by Single Base Extension Methods Oligonucleotides can also be used to detect or type the polymorphisms associated with PRR resistance disclosed herein by single base extension (SBE)-based SNP detection methods. Exemplary oligonucleotides for use in SBE-based SNP detection are provided in Table 19. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 10 in the columns labeled “Forward Primer SEQ ID” and “Reverse Primer SEQ ID”. Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 19

Probes (extension primers) for Single Base Extension (SBE) assays.

| Marker | Marker SEQ ID | SNP Position | SBE Probe | SEQ ID Probe |
|---|---|---|---|---|
| NS0119335 | 8 | 310 | AGACTCTCTCTCTCAGA | 109 |
| NS0119335 | 8 | 310 | ATTGGATTTCTACCCAC | 110 |
| NS0138011 | 10 | 385 | AAATTCCTGTGAATGAA | 111 |
| NS0138011 | 10 | 385 | TTATTCAAAGTAGATTT | 112 |
| NS0119333 | 14 | 607 | TTTTTTAAATTAAGAAC | 113 |
| NS0119333 | 14 | 607 | TGAAAGTGTTGGAGAGG | 114 |

TABLE 19-continued

Probes (extension primers) for Single Base Extension (SBE) assays.

| Marker | Marker SEQ ID | SNP Position | SBE Probe | SEQ ID Probe |
|---|---|---|---|---|
| NS0102262 | 15 | 131 | AAGTACTCCCAAGCCTG | 115 |
| NS0102262 | 15 | 131 | ACAAGACAATCAATTGT | 116 |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A method for introgressing an allele into a soybean plant comprising:
    (a) crossing at least one PRR resistant soybean plant with at least one other soybean plant to form a population;
    (b) screening said population with at least one nucleic acid marker; and
    (c) selecting from said population one or more soybean plants comprising a haplotype associated with PRR resistance, wherein said PRR resistance haplotype corresponding to the Rps1 locus comprises NS0138011, NS0202603 and NS0203225.

2. The method of claim 1, wherein Rps1 comprises Rps1a, Rps1c, and Rps1k.

3. The method of claim 2, wherein the source of Rps1 is elite germplasm.

4. The method of claim 2, wherein the source of Rps1 is accession germplasm.

* * * * *

SEQUENCE LISTING

```
<160> NUMBER OF SEQ ID NOS: 116

<210> SEQ ID NO 1
<211> LENGTH: 845
<212> TYPE: DNA
<213> ORGANISM: Glycine max
<220> FEATURE:
<221> NAME/KEY: UNSURE
<222> LOCATION: (786)..(786)
<223> OTHER INFORMATION: "n= a,t,c, or g"
<220> FEATURE:
<221> NAME/KEY: unsure
<222> LOCATION: (1)..(845)
<223> OTHER INFORMATION: "n= a,t,c, or g"

<400> SEQUENCE: 1
tctaatacag aaagaactca tacaaaattg ctaatatagg ataagttatt ttctatcaca      60
tacactccta ataataattg cctccaatcc atcaatggat ttttcctaac ccacttggat     120
ctcaaatccc atctgatcca catcatacat caatctatac taaaagatta taaagtgtac     180
aagaaattat catgatgcca attgcacaat tggtcaaata ttagatgaaa aaatgagtta     240
tcgctggtat gcaaattttc atcagaacct ggagattaaa ctatagaatg aaaattcaat     300
catacacaaa attttgatcc tttagattga taataagaca aatgtgtagc aacagattta     360
ccttctggca tttatgcaga gaaatttatg agagtgagat ccaatgaaca aataaatgtc     420
tgtgccttta aacacaagta ttggggaagc atcaacacaa gattccatgt aaactttcca     480
aaagttgttc atgtgacctc tgctgcctct tggaacattt gcagaccaag ttgtttggtt     540
tgtatcaatt actgcctgct tccctttata caacaccttg ttgcatcggc taatgagaa      600 tgataatagt gaaggggaat accacgggaa ggattcatca ccccatgatg taacatctat     660
caaacccctc tttaagcgtt tagaaggaaa agaatcatga tcattatctt tcaaaatcat     720
ccttgactca agaggactag aattttcagc atgattcata gaaatatggt tatcttggct     780
ggctgngttt atttgcctac aacaatccag ccttgtatgc aaagagcatg atccttttt      840 ctggg                                                                 845

<210> SEQ ID NO 2
<211> LENGTH: 834
<212> TYPE: DNA
<213> ORGANISM: Glycine max
<220> FEATURE:
<221> NAME/KEY: UNSURE
<222> LOCATION: (796)..(796)
<223> OTHER INFORMATION: "n= a,t,c,or g"
<220> FEATURE:
<221> NAME/KEY: unsure
<222> LOCATION: (1)..(834)
<223> OTHER INFORMATION: "n= a,t,c, or g"
```

<400> SEQUENCE: 2

```
tccatccagg caactcccat tgcttcagta atattccatc ttttaacccg ctccatatca      60
ctagcactcc ttcgctgttc agatgtagcc attgcaacag cactaagacc tcttccagaa     120
ccaatccttg aaaaccgttg aagatcgcga gcagctgcca atgcagcatc tttcgcagct     180
gctttgctct ttggtatctg tgatgttttg ttagggactg ccagaggttt ttgaaagctt     240
gaaaatgaat gaagcctagc atgtttccgt tccagcaatg aggtttcacg cctaatctgc     300
gcatttgacg aaggagcatg attttctgca cctgaagtac cagctgcaat catagacaat     360
gccatcgcag caggtggaga tgcaaaagca gcagcccagg ttggagatat catatcaaga     420
gcagcctgaa agaaattgta agatgcataa ttaagttaat tcaccaaaag tcatacaaat     480
gaatagaaaa tattagcacc atacaatagc tctttatcag cacattactt taactaaact     540
ttgttgggca tgtattattg gagggcaagc aaacaaatac aagtgttcca cttttgatta     600
agttaatgaa aaatttatt atttgaaaat ggtagcagaa agtgttgaaa tgtgatcaag     660
aaaattgaat ttattcttgt aattaggttg aagatttatt cctataatta ggttatttc     720
atttcttaga ataaggaata tttaatgtga tgtggtgtga tttgacttgt cttactaaga     780
gaatgttttg accatntagg aaaaaaaaca aaacaataac tcttgtacaa aacc           834
```

<210> SEQ ID NO 3
<211> LENGTH: 654
<212> TYPE: DNA
<213> ORGANISM: Glycine max

<400> SEQUENCE: 3

```
gccagcttgc atgcctgcag cagctagtgc gcttgccggt gaaggtacgg cacacatgcc      60
aaggctattc agtttttat ctgctgataa ccagggtata gaggcttatt ttcatgctca     120
attttggtt gttgaaattg gttgtggaaa gggaagaaa tccgctttac attttactta     180
tggttttaga ccgcaatgct ggtacttcat tggtcttgaa catacaagca agaatgcaga     240
aagtgaaatt agattatacg tagacgggtc tttatatgaa attcgtcctt tcgagtttcc     300
taggattcc aaaccccttg cattttgctg cataggaact aaccctcctc ctacaatggc     360
tggcttgcaa cgccatcgcc gtcaatgccc tttgtttgct gagatggggc ctgtttacat     420
cttcaaagaa tcaattggac cagaaaggat ggcacgcttg ttttctagag aggggatgt     480
agtaccttct tttggtaatg cagctgggct accatggctc gcaactaatg catatgtgca     540
gagcaaggca gaggaaagtg ttcttttgga tgcagaaatt ggagatttca ttcacctact     600
ctatcatcct agtttgctta gtgggcgttt ctgcccagat gcttcacctt ctgg           654
```

<210> SEQ ID NO 4
<211> LENGTH: 807
<212> TYPE: DNA
<213> ORGANISM: Glycine max

<400> SEQUENCE: 4

```
aagatgctat tggactgttc ctgaaaaaga ttcagtaaat aattttttcac taattggatc      60
aacaagaccg gtgggtgaga tcaatgcttt ggttgacgaa ctcttagtgg taattgaact     120
tctaatagtg gcaggatctc cttcattggt ctcggatgat gtccgatgtt tacttggatt     180
cgtgattgac tgtcgacaac caggtcaggt atgtagtgag atgggatgct tttattctct     240
cttttttgtg ggatagtgaa aataaagtaa aatcttagga aagatgctaa tgatgcacac     300
aaatacaaca ttttagaata tattattatg tcatataata gagaaatact ggatttctaa     360
```

| | |
|---|---:|
| gtaacatcct tctaatttta aaacccaaat tgatatcata aaagtcaatg gttttgttct | 420 |
| tttaggctag tcctgttgtc gttatccaaa ttccagaggt taatcacttt gcttgtgtat | 480 |
| ttcttgttta tgacgggttt ctcttgtaat ttttttatttt ctactttagt tttgtgtttg | 540 |
| aagatttttt agtaagtttt ttattttttta attctctgtt ttcatattgt tttctatttc | 600 |
| taaagtttat acagtaaaaa caactgataa attatttttaa acgtttatta taaagatagt | 660 |
| cttgcaattt taagagaaga aaatgatctt tcttattagt gattgatcag aattacgtga | 720 |
| gagttatata ggaagaaatg gtaaggagag atcctaacca cctgtgcctg aacacaaatt | 780 |
| taatgatctt tcttattatt ctgctgg | 807 |

<210> SEQ ID NO 5
<211> LENGTH: 919
<212> TYPE: DNA
<213> ORGANISM: Glycine max

<400> SEQUENCE: 5

| | |
|---|---:|
| gccattgata caaagtcggt gtacgagaaa gatttcaatg ctttgtcata taaatttatt | 60 |
| gctgttcttg ttgccagttt tgccctagca aggaatatgc agcgatctga ggtttgcctg | 120 |
| ctaactttt ctatggtttt cagattatat tgagataaca tagtatgtta aattcttttt | 180 |
| ttttttcca gattgacagg catgctcgtg caaatataat atgtcagcat cacatcagca | 240 |
| ctggaattca tgcatggcgc aaacttattc gccagtaat cgagatgaga agtctttttg | 300 |
| ggccttttgc ggattatttg taccgcccac ttcgtgtatg tatgatatga ctgtctacat | 360 |
| tgttgctacc aactggcgct ctttgttgct actcatctat ttcttgcctt aaattctcta | 420 |
| atttgttgag tatatgaaaa aactctagga agatgcatat attgattgct gttctttggt | 480 |
| gtatatatat gcctgggaaa aaaaatctaa gaattcaaaa ccaactagtg tagccttttt | 540 |
| gtgcttgtgt tcctagcatt atgtaagggg cttttggctt tgcaaaagag ttagattgct | 600 |
| cttttgaact tatgctcctg ttttctgtt tatgttttct tttcctttg gggatgttct | 660 |
| tggaggattt tttatctatc caactcatgc tttctgatat taaaatcttg ccaaaataat | 720 |
| tttttttaat gattcaatcc accaagctga ttattttcta atttctcta ggttttctgg | 780 |
| aagctagatt ttacggaaag ttcttcccgg atgagaagat gtatgagaag gaattatcaa | 840 |
| ggctctgatc atttaggttt cgctgcgaat tatgaggatt attcagggga gaacaatgat | 900 |
| cacaccactc cagttttat | 919 |

<210> SEQ ID NO 6
<211> LENGTH: 771
<212> TYPE: DNA
<213> ORGANISM: Glycine max

<400> SEQUENCE: 6

| | |
|---|---:|
| aaccgtagct gtatttagtg cgtcggcaaa tgattcaatg tagatccaag ttgcaaatgc | 60 |
| atacccatgg acgaatggcc agcggccctc acctggacca agcaaaccag aactttcgcc | 120 |
| atcaaactcg aaagtgcaag ctggtccaat tgattcctta tcacttactg cttttttccaa | 180 |
| cgcaagcacc aagcgaggtg cccaaattgt ggtaagtgtt cttgtaatga cttgaaacca | 240 |
| tctatgaaga tcactaacac tgagagaatg tgcagccaag tattgtatgc agcggcacaa | 300 |
| aggagttcca tcccacctta tttggccatt taagccaaca tctactgtga aaattttttc | 360 |
| tgctgttctc aacagtattc ccaacaaacc agccatcgag cacatggctc tgtttcgagt | 420 |
| gcatgcccgt aatatggcaa gtagtcccct taccattcgc gtcctgggcg acattgcaac | 480 |

| | |
|---|---|
| atctgaatca cctacataag gaagccaagg aatcagttca cccgacacaa tggccgcccg | 540 |
| agagttcagc attacactag gaggattatc accgtcatct tcaaaacttt caacgccacc | 600 |
| cattgttgca agaagcgaat ccactattaa gaaagacact ctctccattt cttcaccatt | 660 |
| cccgaaaaat tctacaccgc tcgcaatgtt cttcagtttc tccatacctt caggtttccc | 720 |
| catgatagct gaatcaatta agtgcaataa ttctgcaggt cgactctaga g | 771 |

<210> SEQ ID NO 7
<211> LENGTH: 667
<212> TYPE: DNA
<213> ORGANISM: Glycine max

<400> SEQUENCE: 7

| | |
|---|---|
| aaaataacca gattgtttga catgtataca ctgtaatagg actcgggaga aaacaggaat | 60 |
| gaacttacca aaagagtctg ctcaaattga gcacttcgtt taccatctgc tgtaacagca | 120 |
| gtccatccat caggccacat tcgatcccgc cagacaccta ttaataaaca ataatattag | 180 |
| agctgccaca tgtatctatc aaagttatct atttaagaga tattataaag aagtataccg | 240 |
| gcattgatca taggttcaat tgtaaaggtc tgtccggcct tcatcacacc aactgcttta | 300 |
| tttcctgaca gtgattaagg tgtatacatt ccatatgttc tcgttctact ttctagcaac | 360 |
| cttttgttctt tgttaggggg tacgggtaga aaagctagag gtgcacgttg ggaaagaaag | 420 |
| tttggtttaa gaaaaaatgg cacatatgaa tgaggaagct ggctgcttct agcaagtaat | 480 |
| ggtatgtata acagaattgt caataggaag tgaatatata gaatcattcc tagttttgta | 540 |
| agtcatttta tgcgtaaaca aaacaattgg ttgcttagta ttaaaagaga agtatatact | 600 |
| gtgctgaatg ttaaagatca aaacattaga ggatgcaaaa agaaaatttc caaatatttt | 660 |
| tttcaat | 667 |

<210> SEQ ID NO 8
<211> LENGTH: 626
<212> TYPE: DNA
<213> ORGANISM: Glycine max

<400> SEQUENCE: 8

| | |
|---|---|
| tcaaaggaaa ctagaagatt tagcctttca acttaatata aaaatttatc aataaaggat | 60 |
| aatttgttaa ttttttgttaa aaatgtcagg aagatttgaa cttttttattc tttcactctt | 120 |
| tcccaactta ccactgaatt aaccttatat ttccttaata gactcatgga atttcactaa | 180 |
| aaactgcata ggatcaaaat tttcattctg attatttttct tgcttgctac ttttttaaaac | 240 |
| tctggagaag aaaagaataa atatccgaac acgtctgtca tatatattca ctcagactct | 300 |
| ctctctcaga gtgggtagaa atccaataaa gatgacattt atggagctat cactgttttg | 360 |
| acatttatgt tcgcctggag cctttgtaca gccctactgt aacacaagaa cgtacatgct | 420 |
| gcgtagttgg tcctcggcta ccattaccat acaaaactac ctaagaaacc ctactgctct | 480 |
| aagctacatt actactacta ttaactatag attaagagaa ggtagcttat atcttcctca | 540 |
| agctttgtgg ctggtagatg cacagccatg ttttacactt tttactagac atgaaaccaa | 600 |
| tgtcctcctc ctctttcctg cttcta | 626 |

<210> SEQ ID NO 9
<211> LENGTH: 1760
<212> TYPE: DNA
<213> ORGANISM: Glycine max

```
<400> SEQUENCE: 9 tgttttgga attttcctgg ttagaacttg ataggtccat aatgaaggta tataaaagga      60
tagggtctta gtcgaagctt attaatcagt tagaaatctg tttagtagtt agttagttag     120
ttaaaagatg ttagagttag tttcctaaat gtaactgact aaactactca aagcgcttct    180
ctttcctcag caactctgca aagatataaa tgcataataa atgcaacaat aaaaaaaagc    240
tctcatgcag tatttggtca tcttcacgtg ttttacgtag cttactacat tttctctctc    300
tatggcacaa tatgcttatt aatatggtat cagagctctt cttgtgaaga gttctgttgt    360
gccaccgtct ttacgctcac gagtttgcct ttttcatcgt tttctcacca tgaactagtt    420
actactaaac tcaaaaagct atctctatct ccacccaagt gagaacccag ctgttgcact    480
agtttctcca gctttagatt ccagcaatta ccattcatgg agtaggtaca tgataacggc    540
attgagcgcc aagaacaaag tagaattcgt aaacggaaaa gcacccgagc cattgaagtc    600
tgatagaact tacggggcat ggcgtcgctg caacaacatg gtggtatcct ggttagttca    660
ttcagtatcc atctccatta gacaaagtgt cttgtggatg gacaaagcgg aagaaatttg    720
gaatgacttg aaatctcgat acgcacaagg ggaccttttg agagtttctg aactccaaca    780
agaagcttca tccatcaagc aaggatctct ttctattacg gagtatttta caaagctgcg    840
agtcatatgg gacgagatcg aaaacttcat acctgatccc atatgttcat gcactgtcaa    900
gtgtacttgc ttagtactca ccaccatagc tcaacgaaag cgagaagacc gagctatgca    960
gttcctgcaa gggttgaacg aacagtatag caatatatgt tctcatgtgt tgctcatgga   1020
cccaataccc acaataccga aaatcttctc gtacgtggca cagcaggaaa gacaacttac   1080
aggtaacaac tctttatcaa gctttaatct cgaaactaaa gagggacctt ccattaacgc   1140
tgtcaaaagt gtttgtgaat tcggtggacg cattgaccat aatgaaagcg tttgttataa   1200
gaagcacgga ctacctcaga attacgatgg gaaagggaaa agatacaaca caagaaagac   1260
atgtgcctac tgcagaaaac ttggacacac aattgatgtt tgctacaaga aacaagggta   1320
tcccccagga ttcaaattca caatggcaa agcaatagct aacaatgtag tggcagtaga   1380
aggaaaagcc acagatgacc agatactacc ccaagaatct caagaactgg tttgtttctc   1440
accggagcaa tacaaggcac tgctagcttt aatacaacag ccatcggccg gaaactcagc   1500
acccatcaag cctaggtcg cctttatttc atcttgttcc aataacgatg caacaggtat   1560
aattctatct tgcgaaaaag ccaattctac ctcctggatc ttagattcag gagccactga   1620
tcatgtttcc tcctctctaa caaatttca ctcatatcat caaattaatc ccatcacagt   1680
taaactacca aatggtcatc ttgtctatgc tacccactca ggcacaatac aactttctgc   1740
attcattaca ctaaatgatg                                                1760

<210> SEQ ID NO 10
<211> LENGTH: 742
<212> TYPE: DNA
<213> ORGANISM: Glycine max

<400> SEQUENCE: 10
gcgatatgat tccttttct ccagctaaat gataattacc ttctttacag cattgatcca      60
attcacatag atgatcctct ttttccaaca aataatgtgg gaaggaattg cttccgaata    120
catcaatgta ttaaggtatt gattaccaac atgttttcca tatttcagtt ctcatacttg    180
gcctttgcta tgccatgatg acaggaaaaa gaaacctgtg gttgatatta ccacaagct    240 gttaaactat ctgtaattca aaccaataaa aagaaaatc tttcgtttaa ttttggcagt    300
```

| | |
|---|---:|
| aaagcagctt ctaatgtctt tattaactga tcaaggtgtc tataactttt tatgcaataa | 360 |
| tgtgcctgaa attcctgtga atgaaaaatc tactttgaat aacaatgtgg catgtgtcag | 420 |
| cttgatattt tgagaggaaa tgtgttcttg aaagttgtag aggatggaca aattttgttg | 480 |
| gaagtctggc aagccttgtt aacttactgt tagaatttag cttaggacc taattcaacc | 540 |
| ccagaaaact gaattgtaag gtgaggatta tccaagcttt ataagcttta tttaagccac | 600 |
| attccttgtc atgtgggact aaacacaccc tcatgctgg aattaaggca gcccaaagat | 660 |
| gccacaacta aggtgctcta tgggtgacag caattaaggt ggttttccaa cacttatagc | 720 |
| ataattgact ctaaaagatt aa | 742 |

```
<210> SEQ ID NO 11
<211> LENGTH: 878
<212> TYPE: DNA
<213> ORGANISM: Glycine max

<400> SEQUENCE: 11
```

| | |
|---|---:|
| aaaattatgg tataatccga aaaataata atgactacag gaccacccctt tttaatttga | 60 |
| aaatataaag ataacccaga actatcagac caggatctcc tgtatttcat tttttaggt | 120 |
| ttcgaaatat ttaatttgct ctaatgatta agaaaaatgc attttagaac aggacataag | 180 |
| cagctacttc ttcaagggcc aatggagtgg tgaacggaaa acaccaatt ccatatttga | 240 |
| aaactcaata ctcataagaa tgcttaagca taaaagatag tgcaaatcaa tgccagagca | 300 |
| aaaataattc aagttaaaga agccgataat attcagattt cagagtgacg gagaattcca | 360 |
| ttatttccac aactacacca ttcttattcc cttaaattgc taaaaggcaa accttccaaa | 420 |
| aaaatgtcaa ggaaaaccaa aaccaaaacc acaccaaacc ttttgcctag ctcttctaat | 480 |
| actttgacga gcatcttcac atgatttagc aaccaactta gtcatagcct gaaataaatg | 540 |
| tcaaacaaaa aggatatatc agcatgatat atgaaatgag atgtttaaag ggtaaacaat | 600 |
| aattaactgg agtgtaatga gtttacctgc atatgctctt tggtcaatct ggtcatttca | 660 |
| aggtgaagaa gtaaattagt taattaatat tgagcttgaa attcaagttc tttaatagct | 720 |
| attatatcca accaaattca ctcggacagg catgagtaac tgaatgtcaa tagaatacgt | 780 |
| gcttacggtg gaataacagc aatcaatctt tcaccatctg atttaggatt taaccccaat | 840 |
| ggagatgaaa caatagcatt ctctaattgt ttaagtgt | 878 |

```
<210> SEQ ID NO 12
<211> LENGTH: 1388
<212> TYPE: DNA
<213> ORGANISM: Glycine max

<400> SEQUENCE: 12
```

| | |
|---|---:|
| acttgctgac ctgcagggtc tcctctccac aatcctggca aaccaaagaa tgccaccttc | 60 |
| acttctccat cagcatgaat gccagttaaa aagcctcgag attcaggctg agctcctctc | 120 |
| caaccccacc ttggttccac caaaccagtt ctgaacctaa catactgccc aactttaaag | 180 |
| caaggaacct tttcaacttc agtataatga gtcaacaact tcaatttacg gaaacagcaa | 240 |
| gccaactcca gtacccccaga atcctgtaca ctatgcacaa cagctatact tctaacacca | 300 |
| ttcaagtcat tgcttgatct gcttcccggg cttggttttg agcaaaccca atcaccaact | 360 |
| tcaaatcctg gaagttgttc cacatctcca ggagaaacct tccacaagct cttcctacca | 420 |
| gggaccctca cctacaatga aaccaacaaa atcatttatg ccaatagtt taatgatgca | 480 |
| atcacaaata accttgttac caaaatgttg tatgtgaagt ttagcttttt gaacacacaa | 540 |

```
gcagtggcca aaatttcatg tcagtataat tttcacatca tgatgagatc agaaaagaaa      600
tgccagcaaa gctagaaatg gaaagcagtt ttataagaat gtctgattcc ttatactaca      660
actttacatg tgaaaagttt tctgacaaat tccataaata tcctcaactc ttaaccaaca      720
agctacacca ctaggatcag attgaataaa taggcaatca ataatttgca gtcatggttc      780
aattttgagc ttggcatcat tataattcaa tagactcata atctatttga agattacaat      840
agggtttcta tttgaaactt caactttagc gtataaggtg aaaaaaatga attgaatcag      900
tccacccaaa ttaggtgaat tgaatccatg ttagaatata ctccaatgaa ggctaaatcc      960
taggaatgtc tatatggttt tataagcttt ctagcaacag tggaaactgt actggttaca     1020
cttttataag tatgatatct tgcgcaattt tttaataaaa aaaagtaaa tacataaacct     1080 tacattgaga gcaccatcca gatcaattct tgctattttt ccaaaagtag agggtgattc     1140
atttgaccat ccaagccgtg gctggttaac agatggcatc acacgtattt cttgccccgc     1200
ctcaaaatgg ggaactttct caacatcagt gactgagcaa ggaaaaagct tactcctgaa     1260
gcaaaaggca atacccatat cgccatcctc tccaagcta tgaattactc caatgctgtt     1320
tcttgtaaca tcctcccatc catatcttgg agcagacact gaagctttaa ctctgaccca     1380
atctccaa                                                              1388

<210> SEQ ID NO 13
<211> LENGTH: 814
<212> TYPE: DNA
<213> ORGANISM: Glycine max

<400> SEQUENCE: 13
tctaattctt gcttgaattg attaattttg agaggaattt cttttttttt tcttcaaaag       60
cttagcaaaa ttatgattat aaggtatatt ttgtcaaaat aagctaaccc gaatacatac      120
taaatacctc aaggagtttc attaagatag ttccattaga cctgctttct aacttgcaac      180
atgaagaaac ataacctatg aggttggcaa gtactactag caatataaca aagaccatgc      240
taggaacctt cctatgcttg atcatgcggg gaatgagata tcagatggac gaaaagggta      300
agtctgaatt ttggagagtg aaattcggat aggttgagta taagagagaa ggaggggaga      360 taaaggggc acaaaaaggt tgagtgtagt tttggccttt tgggcagtga ggaagcaagc      420
cctctaagtg tctatagtgt ctctatcctt ttcttcttgt tatttctttt acttcttttt      480
acagtagctt ttaacccatt ttctggacta gaatcacact aatatttgat cagattcaga      540
aacatacaga gtatattcag tgaataatac atattttttaa ttccattttc aatcagtaat      600
aactgaatat agtgacaaga aaggaaaag tcaatgaaag agattaaaca attagatctg      660
aaattgcttt ctgacaacaa cctacacaag ttatctttga atagcaaagg cagcactgca      720
ccatttgatg gagcatgaat ttcttgcacg caattattag cttattactt tcagtcgtgt      780
aagaacgtat aaacttactg tgggactccc tcct                                  814

<210> SEQ ID NO 14
<211> LENGTH: 726
<212> TYPE: DNA
<213> ORGANISM: Glycine max

<400> SEQUENCE: 14
atatcagagc ataaggatgt catattaaaa gcaaaaacag aaggaataat actgaaaatg       60
aatccaaaat aggtaggaaa atcttaccct tcatattgca tggtcaccgt gttaccaatg      120
tcagcaaact tacgatcctc aaagattaag aagttatgtt tttctgcaat cttcaacaga      180
```

-continued

| | |
|---|---|
| aagaaacata tattgaaaca actaaaacag aaatgtacta aggttcctga gaactcagta | 240 |
| aacatgttct cataaactta taataggttc aaatgttagc aattcttata acatgctcaa | 300 |
| atgcatcaaa ttctactttc aataaatatt agaaaatcta ctcaagacta taaatgttag | 360 |
| gctgcttta gcactatacc aagcgaagct tagaaccgaa atcaggagta aaatcaggta | 420 |
| aaatatcaac gtgagttttc agcaagcata tctcaggtcc aacctgacat gaagaacaa | 480 |
| ccaaattagt ttaaataatt tttataccag gagtaaactt ctaactataa gtccacaatc | 540 |
| tcactgatga taacaattca gggaacagga atctaacagt tttcaaccca tttttaaat | 600 |
| taagaacccct ctccaacact ttcactgtga ataagtgatc aaacaaaatg ccatggacta | 660 |
| gttaaaaaaa ttcccacttt gtataaatac caagttctta ccttgtcagc aatttcaagc | 720 |
| aattca | 726 |

<210> SEQ ID NO 15
<211> LENGTH: 1337
<212> TYPE: DNA
<213> ORGANISM: Glycine max

<400> SEQUENCE: 15

| | |
|---|---|
| cttgcatgcc tgcacactag aattgaatat ctcacatgta ttgtttcata tgttgtgcac | 60 |
| tttgggtatt atactgaaat gggctttgtc catgcttgct tgggtcaatt attcaagtac | 120 |
| tcccaagcct gacaattgat tgtcttgtct tcaaatgagt aatatgacct tcaaactcag | 180 |
| caacagtagt ggatttagca cattgtagac aaggggccta agtcaaaatt acaaggggcc | 240 |
| taagtcaaaa tttattatta atttattttt ctaatttatt atagtgtttt ttggatacaa | 300 |
| ggggcctaag tcaaaattac aaaagtactt taggcagaaa caaaataccct acaaatttat | 360 |
| tatagtattt gaatatgtaa aaacttgcaa aactcaaatt tgtgtcagtt cagaataata | 420 |
| tttggcttgt tcttctagta atgtacacga ttaattcatc agaaaagttt atgataggaa | 480 |
| aaaaaaaagt aaaaaatatc ttttacctaa gtaattgcag agaacccgtg tagaataaga | 540 |
| agaaaggtat gactaaatat tttataaaac tgataactta ttattttcac aaaataaatt | 600 |
| tcacatccta aacctgaaaa ttgagatcaa tttttattt tatttataa aggaggaaga | 660 |
| ctaatgtctc attttatttt aatattgaga caaaattgta gatagagtaa aataggaata | 720 |
| ttaaaattac attttatcct atttaattt ttgtttgaaa aattaaaaaa aaaagactg | 780 |
| aagaaatata ttcattcaga ttcatccata atcaacaatt aaatcatttc tcatgtcaaa | 840 |
| tactccgtgt ttatctaatt ataagatttt tataaaaaaa tatttatact tttttataaa | 900 |
| aaaaattaat tttagatat attaattatt ttatatatat atattattac ttaattattc | 960 |
| tctgaccaaa cattaataaa aaaataagt aattgaataa aaaaaataat tttaaaatca | 1020 |
| taatataaat aattaacaaa tttaattcga taattacttt taaatattct acaaagccta | 1080 |
| aatgaaaagc agttgggtta ctcgtgtagt cggagtttc acgcaaatga tttccccaaa | 1140 |
| taacaacgcg gcttcccttg atgcctcttc ttctttacct ttttcattgt aattctctct | 1200 |
| cttcactttc tttatctttt cggtttaccc ttacacacgt gcattttctc cttactttt | 1260 |
| ccaccacctt aattcgttat ggcaccacta ttcaaggcct tcgctctctt ctccggcgcc | 1320 |
| gtcgcctgta gccggag | 1337 |

<210> SEQ ID NO 16
<211> LENGTH: 887
<212> TYPE: DNA
<213> ORGANISM: Glycine max

<400> SEQUENCE: 16

```
tgtagttttc aggatagttg gttctggata gagctgatag ttaattctga tttaattccc      60
cttatatgtt gcctggttca aaataatata tgctgaggtg tgattagtta ataaagttga     120
ccttttttta taattaatgt catctatcca tttattttc tattgacctg taagatttaa     180
gcatacacca aaactgtcaa ggaagggggt attctatatc acatgatttt atttcctaaa    240
gaaaaagacc ataaatatag gcatgggaaa gattggagat tagtttgttc atgattctgg    300
ttgaatttcc ttttaaattt ggcattatct gtttcatgat tgtgttcata tgtgggcaga    360
caaatcgaac ttgcaattaa tgatcaattt tttctctttt atttgcagcg ctatgttgaa    420
gctcaatgtt gcatggcttc aaatgattat aaaggttaga tattgtatt tacctggagt     480
cattttgatt attgatttca ttcttgtgtg tttgacgctt ggagctgaag aagtcaaata    540
tgtgtgttgt ggcccttggg ccactttctg acattacaaa atgataattc tactgtaaat    600
tattgtagtg cttatgtggc tcattttct gcattagctt cttgtcttct tgtcttcttg     660
ttttgatcaa acttggacaa tatttaatg agaaaaagt ttttttttt ttggattttc      720
ctatacttgg tagtttctac tatcttcagt gatgtgtgtt tgacactggc acatccagtt    780
ttactttgtt tcaaatgttg gcaggtggat tggaactctt tgcagatctt ttacagcgct    840
tccctaataa tatacacata atacttgaga tggcaaaggt taggctt                   887
```

<210> SEQ ID NO 17
<211> LENGTH: 26
<212> TYPE: DNA
<213> ORGANISM: Artificial Sequence
<220> FEATURE:
<223> OTHER INFORMATION: Other information: Description of artificial sequence: synthetic primer

<400> SEQUENCE: 17

```
tgcacaattg gtcaaatatt agatga                                           26
```

<210> SEQ ID NO 18
<211> LENGTH: 23
<212> TYPE: DNA
<213> ORGANISM: Artificial Sequence
<220> FEATURE:
<223> OTHER INFORMATION: Other information: Description of artificial sequence: synthetic primer

<400> SEQUENCE: 18

```
tccaggttct gatgaaaatt tgc                                              23
```

<210> SEQ ID NO 19
<211> LENGTH: 28
<212> TYPE: DNA
<213> ORGANISM: Artificial Sequence
<220> FEATURE:
<223> OTHER INFORMATION: Other information: Description of artificial sequence: synthetic primer

<400> SEQUENCE: 19

```
tactttaact aaactttgtt gggcatgt                                         28
```

<210> SEQ ID NO 20
<211> LENGTH: 29
<212> TYPE: DNA
<213> ORGANISM: Artificial Sequence
<220> FEATURE:
<223> OTHER INFORMATION: Other information: Description of artificial sequence: synthetic primer

```
<400> SEQUENCE: 20
cattaactta atcaaaagtg gaacacttg                                    29

<210> SEQ ID NO 21
<211> LENGTH: 24
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 21
caagcaagaa tgcagaaagt gaaa                                         24

<210> SEQ ID NO 22
<211> LENGTH: 27
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 22
tcgaaaggac gaatttcata taaagac                                      27

<210> SEQ ID NO 23
<211> LENGTH: 20
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 23
ggcaggatct ccttcattgg                                              20

<210> SEQ ID NO 24
<211> LENGTH: 21
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 24
cgacagtcaa tcacgaatcc a                                            21

<210> SEQ ID NO 25
<211> LENGTH: 19
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 25
tgggcctttt gcggattat                                               19

<210> SEQ ID NO 26
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer
```

<400> SEQUENCE: 26
ggtagcaaca atgtagacag tcatatca                                    28

<210> SEQ ID NO 27
<211> LENGTH: 25
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 27
cgtaatatgg caagtagtcc cctta                                       25

<210> SEQ ID NO 28
<211> LENGTH: 25
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 28
aactgattcc ttggcttcct tatgt                                       25

<210> SEQ ID NO 29
<211> LENGTH: 31
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 29
gcttctagca agtaatggta tgtataacag a                                31

<210> SEQ ID NO 30
<211> LENGTH: 29
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 30
tacgcataaa atgacttaca aaactagga                                   29

<210> SEQ ID NO 31
<211> LENGTH: 27
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 31
ccgaacacgt ctgtcatata tattcac                                     27

<210> SEQ ID NO 32
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer

```
<400> SEQUENCE: 32
cagtgatagc tccataaatg tcatcttt                                          28

<210> SEQ ID NO 33
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 33
gaagagttct gttgtgccac cgtcttta                                          28

<210> SEQ ID NO 34
<211> LENGTH: 30
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 34
gtagtaacta gttcatggtg agaaaacgat                                        30

<210> SEQ ID NO 35
<211> LENGTH: 30
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 35
tttttatgca ataatgtgcc tgaaattcct                                        30

<210> SEQ ID NO 36
<211> LENGTH: 23
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 36
gctgacacat gccacattgt tat                                               23

<210> SEQ ID NO 37
<211> LENGTH: 25
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 37
tcagatttca gagtgacgga gaatt                                             25

<210> SEQ ID NO 38
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer
```

```
<400> SEQUENCE: 38 tttagcaat ttaagggaat aagaatgg                                    28

<210> SEQ ID NO 39
<211> LENGTH: 21
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 39
gccaccttca cttctccatc a                                          21

<210> SEQ ID NO 40
<211> LENGTH: 21
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 40
ggagaggagc tcagcctgaa t                                          21

<210> SEQ ID NO 41
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 41
ctcaaggagt ttcattaaga tagttcca                                   28

<210> SEQ ID NO 42
<211> LENGTH: 25
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 42
tgccaacctc ataggttatg tttct                                      25

<210> SEQ ID NO 43
<211> LENGTH: 26
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 43
ggaatctaac agttttcaac ccattt                                     26

<210> SEQ ID NO 44
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer
```

```
<400> SEQUENCE: 44 gcatttgtt tgatcactta ttcacagt                                    28

<210> SEQ ID NO 45
<211> LENGTH: 23
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 45
atgcttgctt gggtcaatta ttc                                        23

<210> SEQ ID NO 46
<211> LENGTH: 26
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 46
ctgttgctga gtttgaaggt catatt                                     26

<210> SEQ ID NO 47
<211> LENGTH: 29
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 47
gatcaaactt ggacaatatt ttaatgaga                                  29

<210> SEQ ID NO 48
<211> LENGTH: 29
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 48
gtcaaacaca catcactgaa gatagtaga                                  29

<210> SEQ ID NO 49
<211> LENGTH: 13
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 49
ccagcgataa ctc                                                   13

<210> SEQ ID NO 50
<211> LENGTH: 14
<212> TYPE: DNA
<213> ORGANISM: Artificial Sequence
<220> FEATURE:
<223> OTHER INFORMATION: Other information: Description of artificial
      sequence: synthetic probe
```

```
<400> SEQUENCE: 50
accagcaata actc                                                          14

<210> SEQ ID NO 51
<211> LENGTH: 14
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 51
ttggacggca agca                                                          14

<210> SEQ ID NO 52
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 52
attggagggc aagca                                                         15

<210> SEQ ID NO 53
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 53
cgtctacgta taatct                                                        16

<210> SEQ ID NO 54
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 54
ccgtctacat ataatc                                                        16

<210> SEQ ID NO 55
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 55
aacatcggac atcat                                                         15

<210> SEQ ID NO 56
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe
```

```
<400> SEQUENCE: 56
acatcgaaca tcatc                                                      15

<210> SEQ ID NO 57
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 57
ttgtaccgcc cactt                                                      15

<210> SEQ ID NO 58
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 58
tgtactgccc acttc                                                      15

<210> SEQ ID NO 59
<211> LENGTH: 14
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 59
attcgcgtcc tggg                                                       14

<210> SEQ ID NO 60
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 60
attcgtgtcc tgggc                                                      15

<210> SEQ ID NO 61
<211> LENGTH: 18
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 61
caataggaag tgaatata                                                   18

<210> SEQ ID NO 62
<211> LENGTH: 19
<212> TYPE: DNA
<213> ORGANISM: Artificial Sequence
<220> FEATURE:
<223> OTHER INFORMATION: Other information: Description of artificial
      sequence: synthetic probe
```

```
<400> SEQUENCE: 62
agtgaatcta tagaatcat                                              19

<210> SEQ ID NO 63
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 63
ctacccactc tgagaga                                                17

<210> SEQ ID NO 64
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 64
cccacactga gagag                                                  15

<210> SEQ ID NO 65
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 65
ctcacgagtt tgccttt                                                17

<210> SEQ ID NO 66
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 66
ctcacgagtt tgccttt                                                17

<210> SEQ ID NO 67
<211> LENGTH: 22
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 67
tcaaagtaga tttttcattc ac                                          22

<210> SEQ ID NO 68
<211> LENGTH: 19
<212> TYPE: DNA
<213> ORGANISM: Artificial Sequence
<220> FEATURE:
<223> OTHER INFORMATION: Other information: Description of artificial
      sequence: synthetic probe
```

<400> SEQUENCE: 68
aagtagattt gtcattcac                                                    19

<210> SEQ ID NO 69
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 69
agttgttgaa ataatg                                                       16

<210> SEQ ID NO 70
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 70
agttgtggaa ataat                                                        15

<210> SEQ ID NO 71
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 71
atgccagtta aaaag                                                        15

<210> SEQ ID NO 72
<211> LENGTH: 14
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 72
atgccggtta aaaa                                                         14

<210> SEQ ID NO 73
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 73
cctgctttct aacttg                                                       16

<210> SEQ ID NO 74
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 74
tgctttctag cttgca                                                          16

<210> SEQ ID NO 75
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 75
tggagaggtt tcttaat                                                         17

<210> SEQ ID NO 76
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 76
tggagagggt tcttaa                                                          16

<210> SEQ ID NO 77
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 77
caagcctaac aattg                                                           15

<210> SEQ ID NO 78
<211> LENGTH: 14
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 78
agcctgacaa ttga                                                            14

<210> SEQ ID NO 79
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 79
agtataggca aatcc                                                           15

<210> SEQ ID NO 80
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

```
<400> SEQUENCE: 80
aagtatagga aaatcc                                                      16

<210> SEQ ID NO 81
<211> LENGTH: 369
<212> TYPE: DNA
<213> ORGANISM: Glycine max

<400> SEQUENCE: 81
ggacctgctt tttctaatgt gccagctcga gtgcaaccac cagtaccacc acgtaaagtg      60
tgctgtgaaa tttgtaaggt tgagtgcaat agtccagaaa tcttggagca acacaaggtt     120
gggaggaaac atcagaagaa tatgagggtg catgaagaat cgcaaaggcg caatgctata     180
aatggacaac aaagtgggaa aattcctacc tctcaattga atttaacaga ccaacctaag     240
gaagttcagg agtccgagaa aaatgaatgc cccacagaaa atatgggctc ggggggttata    300 atcaatagtc acaaggagga aatgctgctg cagaataatg taggaaacat ttctgaggtt     360
ccagctgaa                                                             369

<210> SEQ ID NO 82
<211> LENGTH: 299
<212> TYPE: DNA
<213> ORGANISM: Glycine max

<400> SEQUENCE: 82
gtgcagctgg gccgaacagc ttgagcatga cgagtcttct tgaagaagca aatctcccgc      60
tggagaccta cctgaagcaa aatggcctta ctagcttgat aacagagcag caaacaaatt     120
cagcttcaaa tgtgcaggca cagacaacca atgatagtga ggtgaaacac aatgaggatt     180
gcggaaccgc tacggttatt catgcgcagg aaagcagccc tgaagagaac agtgggcaag     240
ataaagagca aaacaattaa ctcatgaaat cttgccagtt acattttctt ttttcctttt     299

<210> SEQ ID NO 83
<211> LENGTH: 1008
<212> TYPE: DNA
<213> ORGANISM: Glycine max

<400> SEQUENCE: 83
tgacactgct ttgtacttat tttcttcctt ctttctttgg tctatgaaag atattataat      60
tttaccttga tctcgatctt tccaattcaa ttgtactttc aatcaaatcg cgttttctat     120
gaaattaatt ctcaatattg tgatattata tatgctgagg tatgtgtgag atttttttta     180
tatttttttt tttgtaattt cagaaattct tgttagctca agaagtaccc agcagcaatt     240
cctagttatt ttgcaggaag taaccactc acttaagtta tccttccttc gtcctctaac     300
aatgaaagta atattttttgg ggtatgcaca aagtctttca aaaacaaaca agatctcctg     360
gattgtactc ttattaatta atggagttct gtacatatac atggcatcac acttccaata     420
tagtccaaca aaatggcctt actcctcaat tgccctcttg taattaagat gaaagcacca     480
attgagaggt ggaagcatgg caaacttttt taggtatatg ttctttttga agaaaattt      540 atgcatgaat atatgtcttt tatttttttt tttcctattt tcagactgcg aacaacatca     600
gtatatatga tggttttctc catacgatgt ttccagaagc tagagataca aatgaaaaaa     660
aggttcagga ctgcatatga agggataatt tgaaaagaag aataaagag gaaagatat      720 ttaagtaatt ttttttttct tgaagaaaaa gaaagaaagg aagatatata tatctttaga     780
taaatataat taagggacgt gtaaatatta ttaattgtca aaaaagtaaa gtagcagaga     840
```

```
actacatata gtattacatg caacaacaag cggagacaac taagggactc gcttaagtac      900
tagagtcctc atcgccctct ctttattttc attaatataa attttacaac attatgatat      960
atagtatcct gcgactgaaa aactgccctg caggcatgca agctggcg                  1008
```

<210> SEQ ID NO 84
<211> LENGTH: 1153
<212> TYPE: DNA
<213> ORGANISM: Glycine max

<400> SEQUENCE: 84

```
atggaacacg aaattatagt agaatcatgg tcctacgagg gtagatttcg ctagggttac       60
gaggatggcc aaagtgggtc caaaaggagc agttttgcat gcaagaatgc accaccttac      120
ttaattaatt gcaccttaat gtgggtctat ttgcacactt acctttcaca cgtgttatga      180
atagggccac ctagcagact ttgaactcac tatgaatttc gagttccttc gcgcagtcat      240
gatgaaactc aggtgctcca aattccttaa atttctcaca ctgcaattat aacaacacaa      300
acccaaatta atcatataga aattcgaccc agagatccat tagcaattag tgcaaatctt      360
tttccaagaa tttacaaaat taattaatcg gtgaaattga agaaggggga ttcataatct      420
tggaacgtaa tttagttaca acattcttg ttccatgaaa gaaattaagg ttcttgattt      480
agaataaacg cataattaat tagtgtaaca cccacgttgg ttattttcac acaatttaat      540
attagaaagg ttttataata tgtgtatacc tgctggagat cgagatgctt gaatccatcc      600
atgtccacga cgatctttgc ctaatcctgg aaacaatctt gcaatcttca tctaaatcat      660
atgcaaagaa gaaaagaacg aaacaattaa aatagaatga gtttgtgtgt acctgagaaa      720
tgtacctctc ttcccctctc ctccctcgtc tccactcaga aaatagagca agggaccgtc      780
ctataccctg tagaattcac ctgttcattt attttggaag gctgatgtgt atgcttgatt      840
tgatattttg atagaaccgg tatcttaaca gcgagaaaga atgagttttt tatttaatga      900
aactagggag aagctccttg ggaactaata cactgctttg gatccactcc ttacaccgct      960
ttctcagttt ccaaaagtcc cctatactga ttacactttc cagttattcc tatttatagg     1020
cagcggttgg tttgcagaca taagcacacc cttaatgggc ttaatcagtt gcatgcctgg     1080
tccacttctt gactaacaaa actaaaaccc acaaatagga atgatacctg aaataagtag     1140
ggccatgaat gga                                                        1153
```

<210> SEQ ID NO 85
<211> LENGTH: 18
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 85

```
ccagctcgag tgcaacca                                                     18
```

<210> SEQ ID NO 86
<211> LENGTH: 26
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 86

```
ttctggacta ttgcactcaa ccttac                                            26
```

```
<210> SEQ ID NO 87
<211> LENGTH: 26
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 87
accaatgata gtgaggtgaa acacaa                                              26

<210> SEQ ID NO 88
<211> LENGTH: 25
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 88
ttatcttgcc cactgttctc ttcag                                               25

<210> SEQ ID NO 89
<211> LENGTH: 27
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 89
cactcactta agttatcctt ccttcgt                                             27

<210> SEQ ID NO 90
<211> LENGTH: 31
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 90
aattaataag agtacaatcc aggagatctt g                                        31

<210> SEQ ID NO 91
<211> LENGTH: 24
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 91
ggctgatgtg tatgcttgat ttga                                                24

<210> SEQ ID NO 92
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 92
aaataaaaaa ctcattcttt ctcgctgt                                            28
```

```
<210> SEQ ID NO 93
<211> LENGTH: 18
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 93
ccagtaccac cacgtaaa                                                       18

<210> SEQ ID NO 94
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 94
cagtaccacc gcgtaaa                                                        17

<210> SEQ ID NO 95
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 95
accgctacgg ttatt                                                          15

<210> SEQ ID NO 96
<211> LENGTH: 14
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 96
ccgcttcggt tatt                                                           14

<210> SEQ ID NO 97
<211> LENGTH: 13
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 97
ttgtgcatac ccc                                                            13

<210> SEQ ID NO 98
<211> LENGTH: 13
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 98
ttgtgcagac ccc                                                            13
```

```
<210> SEQ ID NO 99
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 99
atagaaccgg tatctta                                                      17

<210> SEQ ID NO 100
<211> LENGTH: 19
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 100
ttgatagaac tggtatctt                                                    19

<210> SEQ ID NO 101
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 101
tctcagagtg ggtaga                                                       16

<210> SEQ ID NO 102
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 102
tctcagtgtg ggtaga                                                       16

<210> SEQ ID NO 103
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 103
gaatgaaaaa tctact                                                       16

<210> SEQ ID NO 104
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 104
gaatgacaaa tctact                                                       16
```

```
<210> SEQ ID NO 105
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 105
taagaaccct ctccaa                                                        16

<210> SEQ ID NO 106
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 106
taagaaacct ctccaa                                                        16

<210> SEQ ID NO 107
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 107
aagcctgaca attgat                                                        16

<210> SEQ ID NO 108
<211> LENGTH: 16
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 108
aagcctaaca attgat                                                        16

<210> SEQ ID NO 109
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 109
agactctctc tctcaga                                                       17

<210> SEQ ID NO 110
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 110
attggatttc tacccac                                                       17
```

```
<210> SEQ ID NO 111
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 111
aaattcctgt gaatgaa                                                    17

<210> SEQ ID NO 112
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 112
ttattcaaag tagattt                                                    17

<210> SEQ ID NO 113
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 113 tttttttaaat taagaac                                                   17

<210> SEQ ID NO 114
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 114
tgaaagtgtt ggagagg                                                    17

<210> SEQ ID NO 115
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 115
aagtactccc aagcctg                                                    17

<210> SEQ ID NO 116
<211> LENGTH: 17
<212> TYPE: DNA
<213> ORGANISM: Artificial sequence
<220> FEATURE:
<223> OTHER INFORMATION: Other information: Description of artificial
      sequence: synthetic probe

<400> SEQUENCE: 116
acaagacaat caattgt                                                    17
```